(12) United States Patent
Gong et al.

(10) Patent No.: US 7,338,760 B2
(45) Date of Patent: Mar. 4, 2008

(54) SAMPLE PREPARATION INTEGRATED CHIP

(75) Inventors: Haiqing Gong, Singapore (SG); Eric Peng Huat Yap, Singapore (SG); Longqing Chen, Singapore (SG)

(73) Assignees: NTU Ventures Private Limited, Singapore (SG); Defence Science Organization, Singapore (SG)

( * ) Notice: Subject to any disclaimer, the term of this patent is extended or adjusted under 35 U.S.C. 154(b) by 501 days.

(21) Appl. No.: 10/279,627

(22) Filed: Oct. 24, 2002

(65) Prior Publication Data
US 2003/0138941 A1 Jul. 24, 2003

Related U.S. Application Data

(60) Provisional application No. 60/335,875, filed on Oct. 26, 2001.

(51) Int. Cl.
*C12Q 1/68* (2006.01)
*C12M 1/34* (2006.01)

(52) U.S. Cl. ............... 435/6; 435/91.2; 435/287.2; 435/288.5; 435/288.7; 422/102

(58) Field of Classification Search ............. None
See application file for complete search history.

(56) References Cited

U.S. PATENT DOCUMENTS

| | | |
|---|---|---|
| 5,229,297 A | 7/1993 | Schnipelsky et al. |
| 5,368,729 A | 11/1994 | Stefkovich et al. |
| 5,589,350 A | 12/1996 | Bochner |
| 5,948,673 A | 9/1999 | Cottingham |
| 6,045,758 A | 4/2000 | Staples et al. |
| 6,103,479 A | 8/2000 | Taylor |
| 6,110,428 A | 8/2000 | Borst et al. |
| 6,126,899 A | 10/2000 | Woudenberg et al. |
| 6,130,098 A | 10/2000 | Handique et al. |
| 6,143,496 A | 11/2000 | Brown et al. |

(Continued)

FOREIGN PATENT DOCUMENTS

| | | |
|---|---|---|
| CN | 1248702 A | 3/2000 |
| CN | 1254845 A | 5/2000 |

(Continued)

OTHER PUBLICATIONS

Lu, Zuhong et al.; Design and On-Chip Synthesis Technology of Oligonucleotide Microarray; Biomedical Photonics and Optoelectronic Imaging; 2000; pp. 118-121; Beijing, China.

(Continued)

*Primary Examiner*—William H. Beisner
(74) *Attorney, Agent, or Firm*—Knobbe, Martens, Olson & Bear, LLP

(57) ABSTRACT

The present invention relates to an apparatus comprising a substrate having at least one assay station. The at least one assay station has at least a first assay station channel and at least a second assay station channel and the first and second assay station channels each separately being in communication with the at least one assay station. The apparatus has an arrangement of at least first and second multipurpose channels in communication with the first and second assay station channels, respectively. The first multipurpose channel and first assay station channel have internal surface characteristics conducive to conduction of a sample solution therethrough. There is at least one sample fluid inlet in communication with the at least first multipurpose channel, and at least one isolation-medium inlet in communication with the at least first and second multipurpose channels. The at least one second multipurpose channel has an internal surface portion non-conducive to conduction of said sample solution.

62 Claims, 13 Drawing Sheets

U.S. PATENT DOCUMENTS

| | | | |
|---|---|---|---|
| 6,168,948 B1 | 1/2001 | Anderson et al. | |
| 6,180,062 B1 * | 1/2001 | Naka et al. | 422/81 |
| 6,235,471 B1 | 5/2001 | Knapp et al. | 435/6 |
| 6,267,859 B1 | 7/2001 | Kambara | |
| 6,296,020 B1 | 10/2001 | McNeely et al. | |
| 6,306,348 B1 | 10/2001 | Havens et al. | |
| 6,309,602 B1 | 10/2001 | Juncosa et al. | |
| 6,315,953 B1 | 11/2001 | Ackley et al. | |
| 6,319,472 B1 | 11/2001 | Ackley et al. | |
| 6,331,274 B1 | 12/2001 | Ackley et al. | |
| 6,375,899 B1 | 4/2002 | Ackley et al. | |
| 6,379,897 B1 | 4/2002 | Weidenhammer et al. | |
| 6,391,559 B1 | 5/2002 | Brown et al. | |
| 6,391,578 B2 | 5/2002 | Williams et al. | |
| 6,409,832 B2 | 6/2002 | Weigl et al. | |
| 6,426,230 B1 | 7/2002 | Feistel | |
| 2002/0039751 A1 | 4/2002 | Parce et al. | |
| 2002/0055167 A1 | 5/2002 | Pourahmadi et al. | |
| 2002/0106787 A1 | 8/2002 | Benn et al. | |
| 2002/0142471 A1 | 10/2002 | Handique et al. | |
| 2002/0142482 A1 | 10/2002 | Wu et al. | |
| 2002/0143437 A1 | 10/2002 | Handique et al. | |
| 2002/0153046 A1 | 10/2002 | Dantsker et al. | 137/833 |
| 2003/0019522 A1 | 1/2003 | Parunak | |

FOREIGN PATENT DOCUMENTS

| | | | |
|---|---|---|---|
| DE | 19810499 A1 * | 9/1999 | |
| EP | 1 016 864 A2 | 7/2000 | |
| EP | 1 145 760 A2 | 10/2001 | |
| WO | WO 93 22053 | 11/1993 | |
| WO | WO 96 15450 | 5/1996 | |
| WO | WO 99 64840 | 12/1999 | |
| WO | WO 00 22436 | 4/2000 | |
| WO | WO 00 46595 | 8/2000 | |
| WO | WO 00 60352 | 10/2000 | |
| WO | WO 00/62931 A1 | 10/2000 | |
| WO | WO 00 67907 | 11/2000 | |
| WO | WO 01/26799 A1 | 4/2001 | |
| WO | WO 01 41931 A2 | 6/2001 | |
| WO | WO 01 41931 A3 | 6/2001 | |
| WO | WO 02/43864 A2 | 6/2002 | |
| WO | WO 02/059603 A2 | 8/2002 | |
| WO | WO 02/061135 A2 | 8/2002 | |
| WO | WO 02/061858 A2 | 8/2002 | |

OTHER PUBLICATIONS

Kim, Joon Ho et al.; A Disposable DNA Sample Preparation Microfluidic Chip For Nucleic Acid Probe Assay; 2002; pp. 133-136.

Grodzinski, P. et al; Development of Plastic Microfluidic Devices For Sample Preparation; Biomedical Microdevices; 2001; pp. 275-283; Netherlands.

Footz, Tim et al.; Sample Purification on a Microfluidic Device; Electrophoresis; 2001; pp. 3868-3875.

Gourley, Mark F. et al.; Integration of Electro-Optical Mechanical Systems and Medicine: Where Are We and Where Can We Go; Albuquerque, NM; 1997.

Brennan, Thomas M.; Sequencing by Hybridization Methods to Generate Large Arrays of Oligonucleotides; Department of Energy Final Technical Report, Palo Alto, CA Dec. 31, 1996.

Leclair, Tim et al.; Flip Chip Interconnection of DNA Chip Devices; 1998 International Symposium on Microelectronics; pp. 732-736; San Diego, CA.

Kuhr, Werner G. et al.; Direct Detection of DNA With An Integrated Detector On a Microfluidic Chip; pp. 62-63.; Riverside, CA, no date provided.

Yuen, Po Ki, Kricka, Larry J. & Wilding, Peter; Semi-Disposable Microvalves For Use With Microfabricated Devices or Microchips; Journal of Micromechanics and Microengineering; 2000; pp. 401-409; UK.

Lagally, Eric T. & Mathies, Richard A.; Monolithic Integrated PCR Reactor-CE System For DNA Amplification and Analysis to the Single Molecule Limit; $2^{nd}$ Annual International IEEE-EMBS Special Topic Conference on Microtechnologies in Medicine and Biology; May 2-4, 2002; pp. 437-441; Madison, WI.

Boone, Travis D. et. al.; Disposable Plastic Microfluidic Arrays For Applications in Biotechnology; The $11^{th}$ International Conference on Solid-State Sensors and Actuators; Jun. 10-14, 2001.; pp. 1146-1149. Munich, Germany.

McCaman, Michael T. et al.; Analysis of Recombinant Adenoviruses Using an Integrated Microfluidic Chip-Based System; Analytical Biochemistry; 2001; pp. 262-268.

Tang, Thompson et al.; Integrated Microfluidic Electrophoresis System For Analysis of Genetic Materials Using Signal Amplification Methods; Analystical Chemistry; Feb. 15, 2002; pp. 725-733.

Shamansky, Lisa M. et al.; Immobilization and Detection of DNA on Microfluidic Chips; Talanta; 2001; pp. 909-918.

Hicks, Jennifer; Genetics and Drug Discovery Dominate Microarray Research; R&D Magazine; Feb. 1999; pp. 28-33.

Lee, Gwo-Bin et al.; Microfabricated Plastic Chips By Hot Embossing Methods and Their Applications For DNA Separation and Detection; Microfluidic Devices and Systems III; Sep. 18, 2000; pp. 112-121; Santa Clara, CA.

Liu, Robin H.; Highly Parallel Integrated Microfluidic Biochannel Arrays; $14^{th}$ IEEE International Conference on Micro Electro Mechanical Systems; 2001; pp. 439-442; Interlaken Switzerland.

Lu, Zuhong et al.; Design and On-Chip Synthesis Technology of Oligonucleotide Microarray; Biomedial Photonics and Optoelectronic Imaging; 2000; pp. 118-121; Beijing, China.

Hodko, Dalibor et al.; Detection of Pathogens Using On-Chip Electrochemical Analysis of PCR Amplified DNA Molecules; Biomedical Instrumentation Based on Micro- and Nanotechnology; 2001; pp. 65-74.

Blankenstein et al., "Modular Concept of a Laboratory on a Chip for Chemical and Biochemical Analysis," Biosensors & Bioelectronics, vol. 13, No. 3/4, 1998, pp. 427-438.

Waters et al., "Multiple Sample PCR Amplification and Electrophoretic Analysis on a Microship," Anal. Chem., Nov. 6, 1998, vol. 70, No. 24, pp. 5172-5176.

PCT International Search Report for PCT/SG02/00251, completed Jul. 21, 2003, mailed Jul. 29, 2003.

PCT International Search Report for PCT/SG02/00252, completed Jul. 21, 2003, mailed Jul. 29, 2003.

* cited by examiner

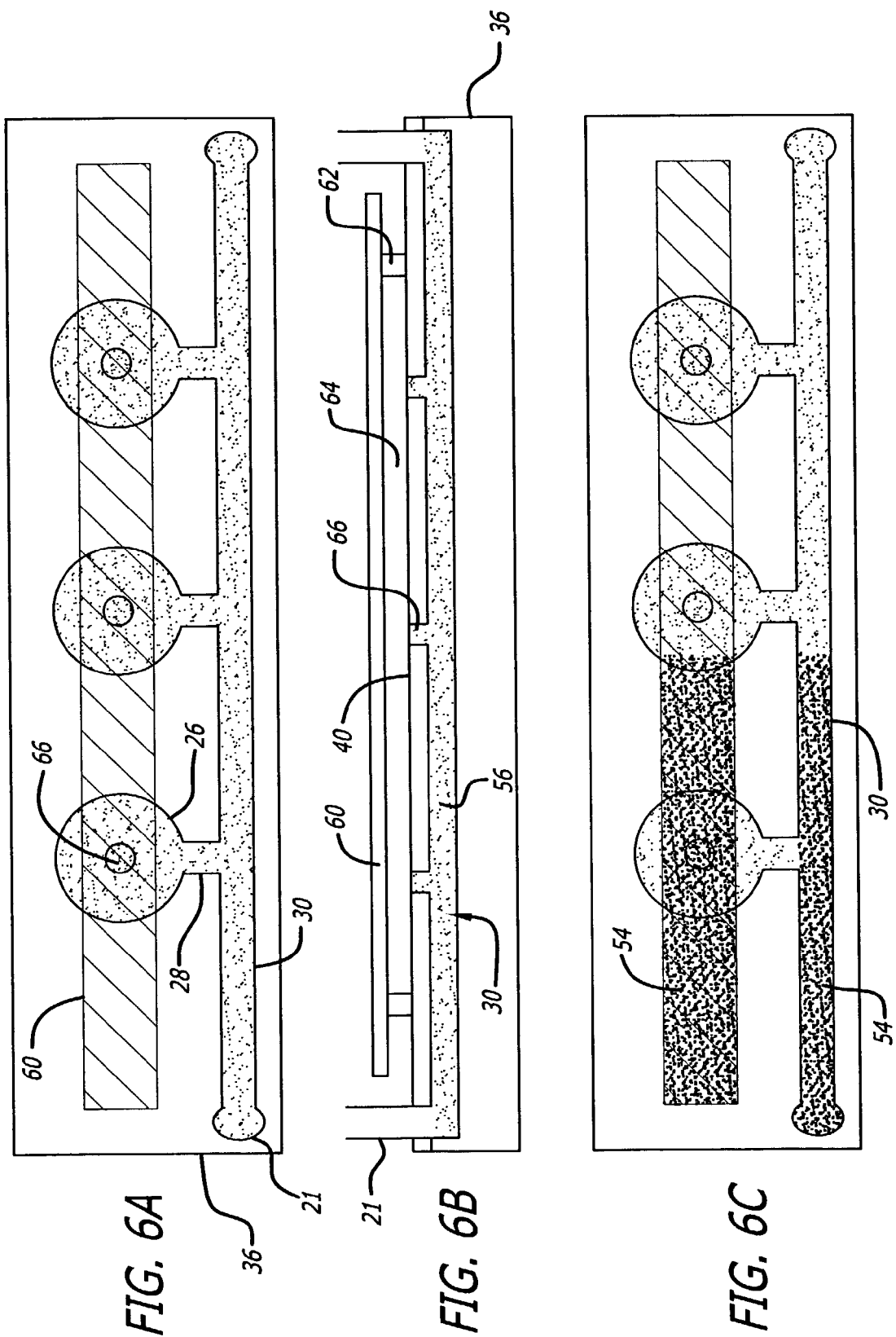

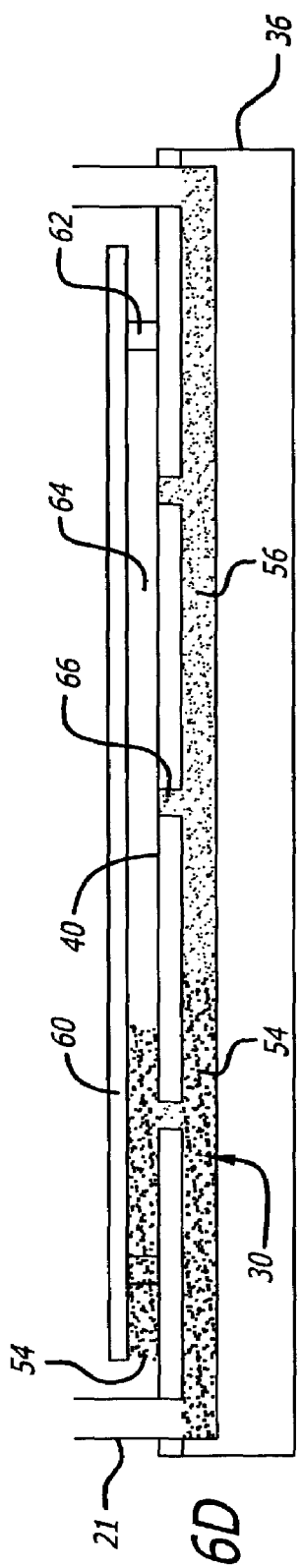
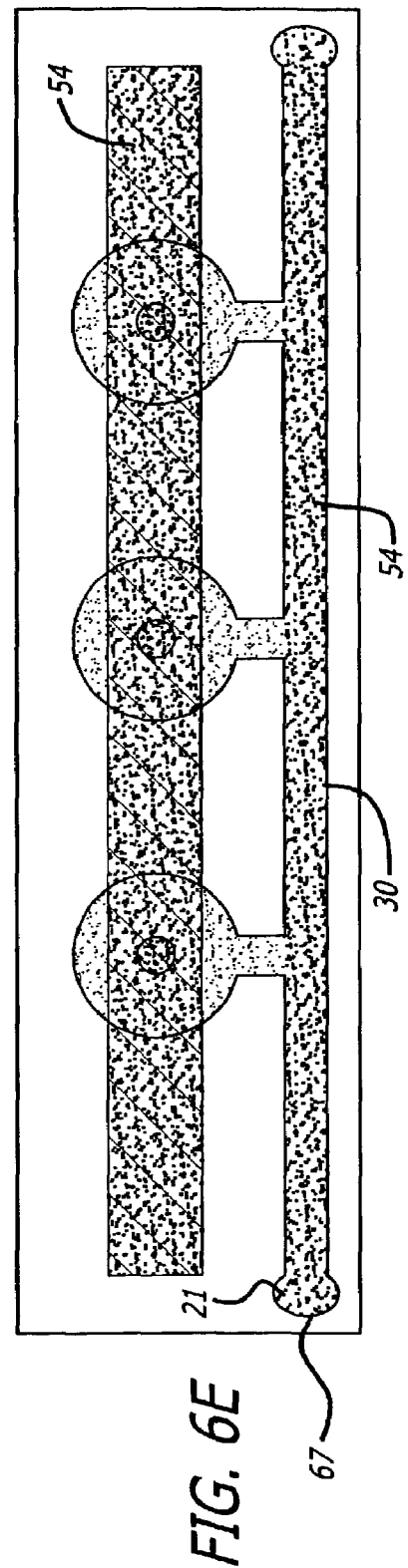
FIG. 6D
FIG. 6E

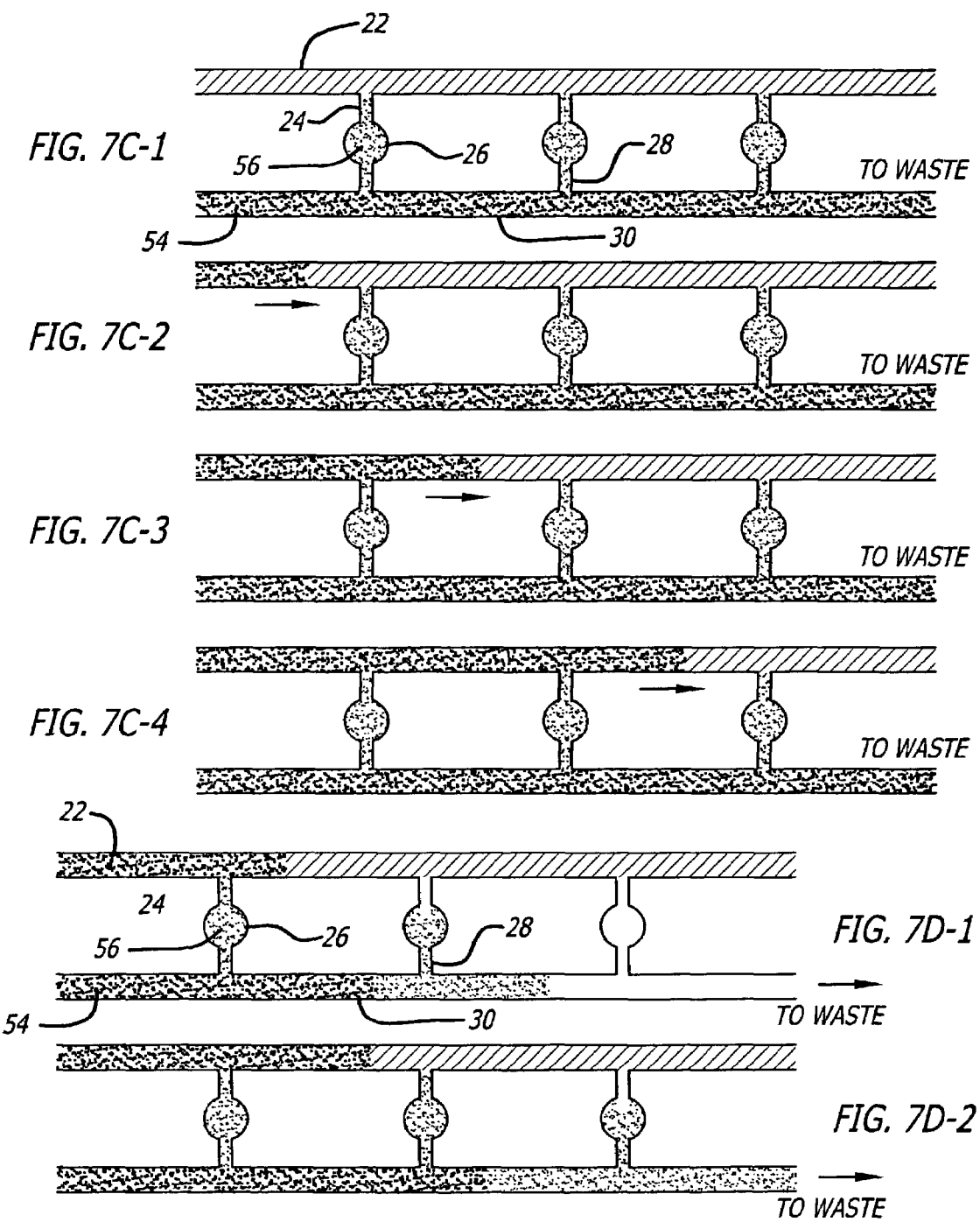

TO WASTE

SAMPLE PREPARATION INTEGRATED CHIP

RELATED APPLICATIONS

This application claims priority to U.S. Provisional Application Serial No. 60/335,875, entitled "Sample Preparation Integrated Chip (SPI Chip) and Analyzer", filed Oct. 26, 2001 and incorporated herein by reference in its entirety.

FIELD OF THE INVENTION

The present invention relates to an apparatus and assay systems which can be employed, for example, for detecting and diagnosing diseases and/or detecting amplified nucleic acid products and/or for pharmacogenetic determinations. The apparatus comprises a substrate with one or more assay stations or wells and channels arranged in a manner to facilitate the flow of fluids through the apparatus and designed to provide for isolation-medium sealing of the assay stations.

BACKGROUND OF THE INVENTION

Biochemical testing is becoming an increasingly important tool for various assays including, for example for detecting and monitoring the presence or absence of diseases. While tests have long been known for obtaining basic medical information such as blood type and transplant compatibility, for example, advances in understanding the biochemistry underlying many diseases have vastly expanded the number of tests which can be performed. Thus, many tests have become available for various analytical purposes, such as detecting pathogens, diagnosing and monitoring disease, detecting and monitoring changes in health, and monitoring drug therapy. Genomic data in conjunction with the ability to prepare combinatorial libraries of chemical components has facilitated the discovery of new drugs.

There has long been a need for "complete systems" allowing various stages of nucleic acid, e.g., DNA, analysis to be performed on a single device, such as a microchip. Fully integrated, high throughput systems are needed which rapidly and simultaneously perform DNA analyses such as DNA separation and PCR and thereby permit disease diagnosis or detection. Sanders, et al. (2000) *Trends in Analytical Chemistry*, 19(6): 364-378. Systems where up to four samples can be amplified and analyzed on the same chip have been previously disclosed. L. C. Waters, et al. (1998) *Anal. Chem.*, 70: 5172. In addition, small, disposable mass-produced devices for conducting PCR have been reported; see e.g. U.S. Pat. No. 5,498,392. For example, Yuen, et al. (2001) *Genome Research* 11:405-412, provides a plexiglass-based microchip module designed and constructed for the integration of blood sample preparation and nucleic acid amplification reactions. The microchip module comprises a micro heater-cooler and a series of microchannels for transporting human whole blood and reagents. The white blood cells are first isolated from a small volume of whole blood in integrated cell isolation-PCR containing gate-like microstructures which retain white blood cells, albeit at a very low concentration and efficiency (i.e. 3-5%). Red blood cells pass through the micro-filters but tend to clog up the filters over time causing inefficiencies in white blood cell isolation. The Yuen, et al. microchip employs a microtemperature sensor, making the Yuen, et al. chip expensive to fabricate.

DNA microarray devices are also currently employed for DNA analysis. Two types of DNA microarray technologies are known, cDNA microarray and oligo microarray. Both technologies examine the mRNA expression in a sample based on hybridization reactions. The microarray-based assays are cumbersome, taking about a day to complete and requiring standalone equipment to conduct sequential batch analyses. Rapid diagnoses are precluded and current microarray devices do not permit sample preparation to be integrated onto the chip.

Additional disadvantages of the current on-chip DNA analysis systems have recently been reported. Such disadvantages include lack of sample injection ability, poor DNA isolation and inability to conduct multiple PCR analyses. Yuen, et al. Page 4005, right column.

Nucleic acids play a direct role in cellular processes, including those resulting in disease states by functioning in the control and regulation of gene expression. Hybridization techniques have been developed to conduct various types of nucleic acid analyses to better understand how genetic information functions in diverse types of biological processes. Hybridization methods generally employ the binding of certain target nucleic acids by nucleic acid probes under controlled conditions thereby enabling hybridization to occur only between complementary sequences. Using hybridization techniques, it is possible to conduct gene expression studies as well as a variety of other types of analysis. For example, gene expression studies are important because differential expression of genes has been shown to be associated with disease states. Many disease states have been characterized by differences in the expression of various genes either through change in copy number of the genetic DNA or through alterations in levels of transcription. In certain diseases, infection by a particular virus is characterized by elevated expression of genes.

Chips to which nucleic acid probes are attached can be used to conduct nucleic acid analyses. Probes can be attached at specific sites on the chip, such as assay stations. Assay stations are situated in areas intermediate between first and second multi-purpose channels, wherein assay reactions are run, as detailed below. In some applications, the chip may include assay stations arranged in the form of an array. Genetic methods utilizing arrays on chips are advantageous because such chips allow for simultaneous, parallel processing that can increase the rate at which analyses can be conducted as compared to conventional methods which often require labor intensive sample preparations and electrophoretic separations. Current nucleic acid methods using chips typically require complex off-chip sample DNA isolation, integrated micro-heaters and micro-temperature sensors for PCR thus making current chips and associated methods of using same very expensive and non-disposable.

It is an object of this invention to provide disposable microchips permitting multiples of assay stations for carrying out various biochemical assays in real-time.

SUMMARY OF THE INVENTION

The present invention is directed to a microchip apparatus and assay systems useful, for example, for detecting and diagnosing the presence of absence of diseases in a subject and/or for detecting amplified nucleic acid products or for pharmacogenetic determinations. The apparatus comprises a substrate with one or assay stations and channels which are designed and arranged in a manner which facilitates the introduction and flow of sample fluid and isolation-medium.

The apparatus can also include an integral sample preparation portion and the invention provides an improved result detection system.

The present invention relates to a microchip apparatus on which numerous types of assays can be performed. Use of the term "assay" herein is meant to describe any qualitative or quantitative analysis of a substance that is examined by trial or experiment, including reactions that indicate the absence of a particular substance, such as, but not limited to, a protein, antibody, nucleic acid fragment as well as any indicator or marker typically utilized in the art for particular assays. The instant microchips generally comprise at least one assay station wherein each assay station may communicate with a first and second assay station channel. Also provided are multi-purpose channels in communication with the assay station through which sample solution and/or isolation medium can be introduced and conducted through the microchip.

An embodiment of the present invention is directed to an apparatus for detecting a disease comprising a substrate, the substrate having embedded in the substrate: a sample preparation chamber which may be configured for filtering white blood cells; a sample introduction inlet fluidically coupled to said sample preparation chamber; a buffer introduction inlet fluidically coupled to the sample preparation chamber; a flow-promoting fluid chamber, a storage chamber for storing flow-promoting fluid, the storage chamber fluidically coupled to the flow-promoting fluid chamber; and the sample preparation chamber fluidically coupled to the flow-promoting fluid chamber. The present invention can further comprise an isolation device for isolating and permitting flow of a fluid from the sample preparation chamber to the flow-promoting fluid chamber; a first multi purpose distribution channel fluidically coupled to the flow-promoting fluid chamber; at least one assay station; the first multi purpose channel fluidically coupled to the assay station; and an isolation device for isolating and permitting flow of a fluid from the flow-promoting fluid chamber to the assay station/plurality of assay stations. Further there may be provided at least one buffer introduction inlet, the buffer introduction inlet fluidically coupled to the first multi purpose channel; second multi-purpose channel, the second multi-purpose channel fluidically coupled to the assay station; and an inlet which may provide venting, with the inlet fluidically coupled to the second multi-purpose channel. The sample preparation chamber, the storage chamber, the flow-promoting fluid chamber, the assay station, and the channels, may be embedded within the substrate and can be, if desirable, sealed from the environment.

In another aspect of the invention, the flow-promoting fluid chamber, and associated channels, and the storage chamber are omitted and the functions performed in those chambers are instead performed in the sample preparation chamber.

The foregoing apparatus can be employed to carry out the method of the present invention of detecting a presence or absence of a disease state. An exemplary method is directed to detecting a presence or absence of a disease state, in a test sample from a subject such as, for example, an organism such as, but not limited to, animals, plants and other living organisms. The method comprises the steps of: (a) with the isolating device in the isolating position, depositing a specific DNA fragment in the assay station and drying the assay station; (b) applying a sealing layer to the assay station; (c) injecting into the sample introduction inlet a biological blood sample; (d) injecting a washing buffer into the buffer introduction inlet to form a mixture of the sample of blood and the washing buffer in the sample preparation chamber; (e) causing red cells to separate from white blood cells, therein leaving said white blood cells in the sample preparation chamber; (f) injecting a lysing buffer into the buffer introduction inlet to lyse the white blood cells containing DNA fragments into solution in the lysing buffer; (g) injecting a gas into the sample preparation chamber, thereby pushing the lysing buffer into the flow-promoting fluid chamber; (h) diffusing a chemical from the chemical storage chamber into the flow-promoting fluid chamber; (i) causing the isolation device to permit flow of the lysing buffer containing DNA fragments into the first multi purpose channel to the assay station; (j) detecting when the assay station is filled with the lysing buffer containing the DNA fragments; (k) amplifying the DNA fragments; and (l) detecting the amplified DNA fragments.

BRIEF DESCRIPTION OF THE DRAWINGS

FIGS. 6A-E show another exemplary embodiment of a microfluidic chip made in accordance with the teachings of the present invention providing another sealing arrangement;

FIGS. 7A-1-7A-4 show an exemplary sequence of filling a plurality of assay stations with sample fluid;

FIGS. 7B-1-7B-4 show the displacement of sample fluid by an isolation medium and sealing on one side of a plurality of assay stations;

FIGS. 7C-1-7C-4 show the sealing of another side of a plurality of assay stations by an isolation medium;

FIGS. 7D-1-2 shows another exemplary sequence of filling and sealing a plurality of assay stations;

FIG. 1B is a top plan view of sample fluid preparatory area of FIG. 1A;

DETAILED DESCRIPTION OF THE INVENTION

Figure 1:
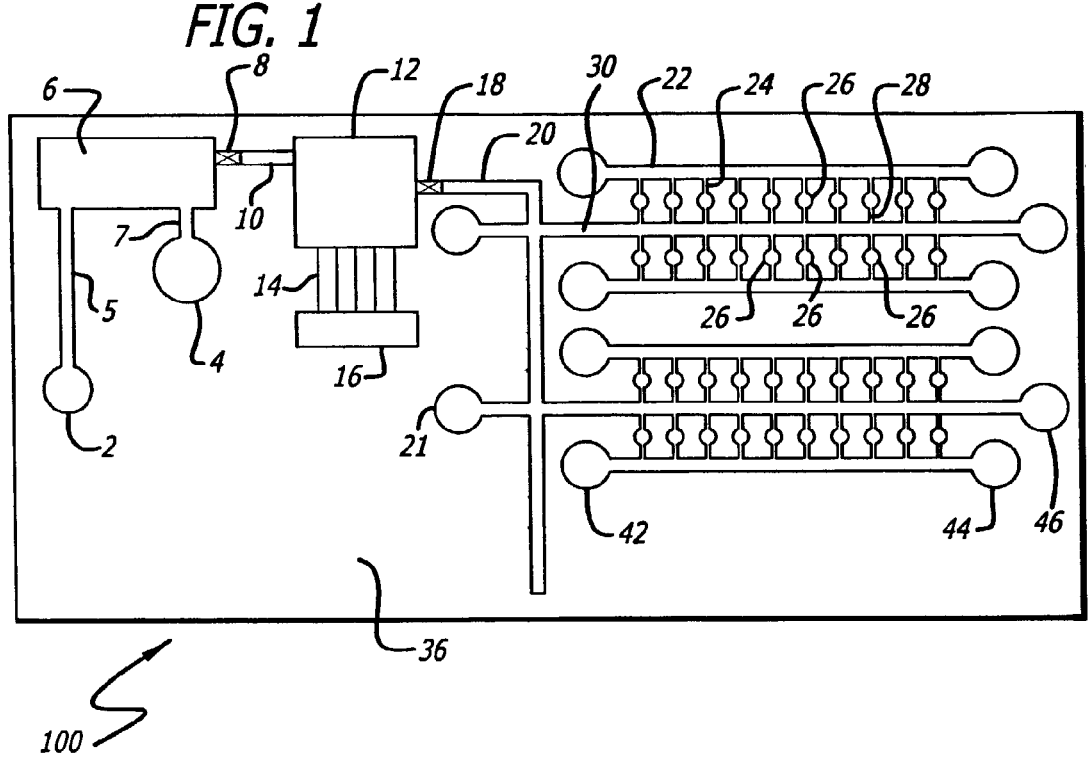
FIG. 1 is a plan view of the upper surface of an exemplary sample preparation integrated (SPI) chip in accordance with the teachings of the present invention.

The present invention relates to an apparatus comprising a substrate having at least one assay station in which the at least one assay station has at least a first assay station channel and in particular embodiments may have at least a second assay station channel. As utilized herein, the term assay station describes the area at which a particular assay takes place. In particular embodiments, an assay station comprises an area bounded by isolation medium, for example. The said first and second assay station channels each separately are in communication with said at least one assay station. An arrangement of at least first and second multi-purpose channels are provided which are in fluid communication with said assay station. The first multi-purpose channel and first assay station channel have internal surface characteristics conducive to conduction of a sample solution therethrough. For example, if an aqueous fluid sample is provided, the channels may be either hydrophilic or are treated so as to be hydrophilic. In particular embodiments, the shape of particular channels (geometric characteristic) provides particular conducive or non-conducive characteristics to particular channels, particularly when channels having different relative geometric characteristics are in communication.

At least one sample fluid inlet is in communication with the at least first multi-purpose channel, and at least one isolation-medium inlet is in communication with the at least first and second multi-purpose channels. The at least one second multi-purpose channel has at least an internal surface portion non-conducive to conduction of said sample solution. For example, if the sample fluid is aqueous, the second multipurpose channel inner surface would be hydrophobic or would be treated so as to be hydrophobic.

The apparatus can further comprise a sealing layer which seals at least one assay station. If desired the sealing layer can seal only the at least one assay stations or can seal portions of the apparatus substrate up to and including the entire substrate surface.

In one embodiment, the internal surface of said first multi-purpose channel permits flowthrough of at least one of a sample fluid, air and an isolation-medium and the internal surface of said second multi-purpose channel permits the flowthrough of at least one of air or an isolation-medium but is not conducive to flowthrough the sample fluid.

In another embodiment of the invention, the internal surface of the multi-purpose channel and/or a surface of the second assay station channel immediately adjacent to the intersection of the second assay station channel and the second multi-purpose channel are both non-conducive to conduction of said sample fluid. This embodiment further assists in the localization of sample fluid to the assay station as well as the sealing and isolation of the assay station.

The substrate can be configured such that at least first and second multi-purpose channels are in communication with a plurality of assay stations via the first and second assay station channels, respectively, of said plurality of assay stations. The plurality of assay stations are arranged to provide at least one of simultaneous or sequential filling of the plurality of assay stations with the sample fluid solution conducted thereto via the at least first multi-purpose channels and the first assay station channels. Additionally, the plurality of assay stations can be arranged to provide at least one of simultaneous or sequential filling of the first and second multi-purpose channels with the isolation medium to seal the plurality of assay stations.

The assay stations can have disposed therein at least one reaction assay component. For example, if PCR is contemplated, the reaction assay component can be one or more primers and/or a probe.

A sample fluid inlet can be in communication with a sample fluid preparation area and the substrate can include at least one of a sample preparation chamber which may or may not have a lid. At least one element for controlling fluid flow in at least one of said channels can be incorporated into the apparatus or substrate.

The flow of sample fluid in the channels on the substrate can be facilitated by the introduction of a flow-promoting fluid in to the sample fluid via a chamber for introduction of flow-promoting fluid.

The chamber can be in communication with a chamber for mixing said flow-promoting fluid with the sample solution.

The present invention further comprise a method for conducting reactions on the substrates of this invention.

An exemplary method includes introducing a sample fluid to at least one sample inlet; filling the at least one assay station and the second assay station channel via the at least one multi-purpose channel; allowing isolation-medium from the at least one isolation medium inlet to flow into at least the first multi-purpose channel; and running at least one reaction at said at least one assay station. The reaction in the assay station provides at least one of qualitative or quantitative data, for example, a colormetric result. The at least one of qualitative or quantitative data can be obtained utilizing fluorecence which can be provided by at least one of intercalation of a flurophore or fluorecently labeled probe. When fluorescence is employed, the assay stations in the substrate can be irradicated with at least one excitation frequency. The probe can be labeled by at least one of a flurophore, an enzyme or component of a binding complex. The result of this method provides at least one of qualitative or quantitative data relating to the sample fluid being assayed. Exemplary qualitative or quantitative may be exemplarily provided by florescence resonance energy transfer, luminescence or colorimetric change, for example.

If desired, the reactions conducted on the substrate can be conducted under temperature control, for example, thermocycling conditions. The test sample can be provided to the apparatus by initially subjecting the test sample to at least one preparative operation. The preparative operation can be performed separately from said substrate or can be performed at at least one preparative station which is upon or within the substrate.

The at least one preparative operation can, for example, provide nucleic acids susceptible for use in the reactions to be conducted in the assay stations on the substrate.

Additionally, at least one assay reaction component can be disposed or placed into the at least one assay stations. The reactions may provide for the detection of a variation in nucleic acid sequence that is associated with virulence, disease, a particular phenotype or interindividual or interspecific variations or differences. Such variations in nucleic acid sequences include single nucleotide polymorphisms (SNPs), tandem repeats and insertions and/or deletions.

The at least one reaction which can be conducted includes a nucleic acid amplification step, and the assay reaction component might in that case include a primer or primers.

The method of the invention provides for sealing or isolation of the assays stations by displacement of sample fluid in the multi-purpose channels by an isolation-medium. The isolation-medium can be introduced sequentially into the at least first and second multi-purpose channels or isolation medium can be first introduced into the at least first multipurpose channel followed by introduction into the at least second multipurpose channel. The isolation-medium is typically a material which is of an opposite nature as compared to the sample fluid, that is, substantially immiscible with the sample fluid.

The introduction of isolation medium provides the purging of air from said at least second multipurpose channel and the purging of said sample fluid from said at least first multipurpose channel, resulting in the isolation of said at least one assay station containing said sample isolation. In the case where the isolation medium is solidifiable, the instant method includes a step of at least one of solidifying, curing and polymerizing said isolation medium.

A particular but not limiting embodiment of the present invention is directed to sample-preparation integrated, disposable, microfluidic devices and methods of using such devices. The devices and methods of the present invention facilitate analysis of nucleic acids, e.g. DNA, to rapidly detect and/or assess the risk of diseases in biological samples. The devices of the present invention can also be used for detecting amplified nucleic acid products for e.g. pharmacogenetic determinations such as for genetic fingerprinting. As used herein the term "detect" or "detection" or "detecting" means to diagnose or indicate that a subject test sample contains at least one disease-associated nucleic acid. By "device" is meant a chip which incorporates elements necessary to transport nucleic acids and perform nucleic acid amplification, such as polymerase chain reaction (PCR). The device can optionally incorporate elements necessary for on-chip isolation of nucleic acids, such as a micro-filter, sized to trap white blood cells from a human blood sample, for example. In accordance with the present invention, DNA molecules can be rapidly analyzed from a test sample, e.g. a biological sample. In one embodiment, once applied to the device, the test sample is assayed to determine the presence or absence of a disease or assess the risk for developing a disease. A "test sample" employed by the present invention includes animal tissue and blood. The test sample is preferably whole blood. In one embodiment, a tissue homogenate or blood sample from a subject is tested in the assay system of the invention. Where a tissue sample is to be assayed by the device and methods of the present invention, the tissue sample is conventionally homogenized, digested and filtered to remove solid debris and obtain DNA in a solution which can be applied to the device of the invention.

For example, the presence of infectious pathogens (viruses, bacteria, fungi, protozoans, microbial organisms or the like) or cancerous tumors can be detected by providing a virus-specific primer or cDNA or fragment, pre-labeled with a fluorescent molecule such as fluorescein. The test sample DNA is conducted through the device to the primer where a fluorescent signal will be produced if the test sample contains the disease-causing virus, following PCR.

Biological test samples in accordance with the present invention are derived from subjects using well-known techniques such as venipuncture or tissue biopsy. Where the biological test sample is derived from non-human animals, such as livestock, blood and tissue samples are generally obtainable from livestock processing plants. Depending upon the particular embodiment being practiced, the test compounds are provided, e.g. injected, or optionally free in solution. Animals contemplated by the present invention include, for example, humans, reptiles, livestock, avian species, and domesticated pets such as dogs and cats. A preferred animal is a human being.

According to the present invention, the device is a lab-on-a-chip which can have various channel dimensions (i.e. lengths, widths, heights, diameters). For example, the multipurpose channels may have lengths of about 1 mm to about 500 mm in length, from about 2 mm to about 10 mm in width, from about 0.5 mm to about 10 mm in thickness. The assay station channels may have similar dimensions and have exemplary lengths of about 0.01 mm to about 50 mm. A sample preparation area may be about 5 to about 100 mm in length and width and about 0.5 mm to about 10 mm in height. The device can contain one or more sample introduction inlets, one or more chambers, one or more interconnected channels (sized to accommodate fluid flow) with surface of entire channels or a part of channels being selectively either inherently hydrophobic or hydrophilic or can be treated with hydrophobic or hydrophilic materials, and one or more assay stations for nucleic acid (e.g., DNA and RNA) amplification. The device also preferably contains at least one nucleic acid-adsorbant surface, such as a silica-derivitized surface. The device may alternatively contain at least one membrane filter for separating white blood cells from a test sample. In one embodiment, the methods of the present invention are carried out on the device following extraction of a biological test sample for substantially immediate detection results. By "substantially immediate" is meant results can be obtained in about 5 minutes to 2 about hours. In another embodiment, the present invention also contemplates sample pre-processing off-chip and storage of the test sample, if processing is desired at a later time. Pre-processing is generally employed when the test sample is obtained from flow cell sorting devices or centrifugation devices, and the like. Sample preparation protocols for DNA or RNA can be found in Sambrook et. al., Molecular Cloning, A Laboratory Manual, 2nd edition. and/or be accomplished with kits from Qiagen, Whatman, etc., which utilize columns/membrane to bind DNA.

For pre-processing, non-nucleic acid molecules that may inhibit subsequent amplification or interfere with the fluorescent analysis of products are removed. Pre-processing is conventionally performed in a device which can be modular and separate from the device of the present invention. The pre-processing module contemplated to mate with and/or fluidically attach to the device of the present invention is a stand alone module. The stand alone module is linked by a liquid delivery tube which can connect to sample inlet 2 of the device of the present invention.

Preferably, pre-processing is performed on-chip. In accordance with the present invention, for pre-processing of a test sample, DNA and/or RNA is separated from other biological macromolecules and small molecules in crude samples such as body fluids (including blood, feces, sputum, aspirates, swabs), homogenized tissues samples (hair, mouth swabs, biopsies, aspirates, whole organisms), environmental samples (surface swabs, food, water/liquids) and the like. These samples can also be enriched and semi-purified. For example, the present invention contemplates enriched or semi-purified populations of: white cells after buffy coat centrifugation separation; cells cultured in vitro and cells obtained after flow sorting. Preprocessing is performed off-chip to disintegrate large pieces by the standard procedure of aspirating the solid sample through a fine-bore needle such as a 21G-28G sized needle, for example. The sample can be stored in standard chemicals, such as guanidium isothiocyanate, for example, to inhibit the degradation of DNA or RNA if sample processing cannot take place immediately.

In accordance with aspects of the present invention, DNA and/or RNA is isolated from a test sample. The DNA and/or RNA is adsorbed onto a derivitized silica surface immobilized on the microdevice in the presence of appropriate buffers such as guanidium isothiocyanate and $NH_4Cl$ dissolved in water and Tris-HCl adjusted to pH 7.2, for example. The nucleic acids adhere to the surface due to electrostatic charges. The adsorbent surfaces contemplated by the present invention include: particle beads (glass beads) held in chambers with filters; paramagnetic particles immobilized in chambers by magnetic fields; and membranes or filters allowing liquids to pass through based on ionic charge properties.

Immobilized or trapped nucleic acids are conventionally washed to remove unwanted cellular debris and macromolecules. The DNA/RNA is then eluted by changing the charge of surface and/or nucleic acid using buffer of neutral pH (including water), either by forward-flow or by back-flushing. The fluidics of sample introduction, washing and elution are carried out using passive or active valves and pumps, negative pressure suction or positive pressure. Preferably, test samples are introduced into the device using one or more pumps, such as syringe pumps, manual syringes, peristaltic pumps or vacuum pumps.

In accordance with one aspect of the present invention, nucleic acids are amplified at assay stations. A digital camera having a sensing element and suitable optics for acquiring images can be employed to detect light of specific wavelengths emitted from the samples in the wells. Nucleic acids are selectively amplified to sufficient quantities for direct and simultaneous detection without or with minimal post-amplification steps.

Amplification reactions contemplated by the present invention include, for example, polymerase chain reaction, ligase chain reaction or isothermal amplification reactions. In one embodiment, a reverse-transcription step (employing enzymes capable of reverse transcription) for amplifying RNA targets is conducted before the main amplification step. In another embodiment a reverse transcription step is combined with the DNA amplification step.

In accordance with the present invention, nucleic acids are introduced into the assay stations together with conventional reagents for the amplification reaction such as enzymes, primers, deoxyribonucleotide triphosphates dNTPs, fluorescent dyes, detergents, salts and buffers. In an alternative embodiment, some of the reagents (particularly primers and/or probes) may be pre-applied to the assay station and dried; these reagents will be solubilized on contact with the incoming sample/reagent liquid mix. A second liquid in characteristic, immiscible phase such as Mineral oil, wax, and the like, can be added to the chip through one or more channels after the sample/reagent mixture. The immiscible liquid will "seal off" fluidic access to the assay stations and act as a physical barrier to prevent the unwanted mixing of the contents of the assay station with that of adjacent assay stations.

The assay stations on the device of the present invention can be arrayed in high density, either in two-dimensions or in three-dimensions, with each having an exemplary volume ranging from about 1 pico liter to about 50 micro liters. The present invention has the capacity to simultaneously amplify and detect nucleic acids present in about 10 to about 50,000 assay stations. The present invention also contemplates the inclusion of individualized thermal controls for each assay stations. In a preferred embodiment, the assay stations are subjected to common thermal parameters. Common thermal parameters permit the reactions in each assay station to be optimized to a single set of thermal conditions by varying the design of the amplification reaction, or the concentrations of the reagents. For example, the amplification reaction may take place either by cycling through a set of predetermined temperatures for example, 95° C. for denaturation, 50-60° C. for primer annealing, with or without a 72° C. extension step. Preferably, the amplification reaction is conducted isothermally at a constant temperature (e.g. 60° C.).

In accordance with the present invention, the products of DNA amplification are detected in situ homogeneously by detecting fluorescence emitted specifically in the presence of amplified DNA product. Detection is achieved using a fluorophore that specifically fluoresces on binding with double-strand DNA such as ethidium bromide or SYBR Green I, for example. Alternatively, a specific DNA sequence can be detected using one or two fluorophore-labeled oligonucleotide probes using transfer of fluorescent resonance energy. In one embodiment, the detection step can be performed after the complete amplification process. In another embodiment, the detection step can be performed after individual thermal cycles. In still another embodiment, the detection step can be performed during intermediate points of an isothermal reaction. The detection of amplified nucleic acids is performed with a digital camera using excitation from an off-chip source of incident UW or other appropriate wavelength light, and off-chip detectors for the emitted wavelength. The results of detecting amplified DNA products are used in comparison against a pre-amplification baseline which is experimentally determined by the fluorescent emission reading within the experiment obtained at amplification cycle zero. Alternatively, the pre-amplification baseline is determined with respect to different fluorescent probes at the same assay station, or with probes from the reactions of different assay stations.

It is preferred that all methods of the present invention are carried out on the device. The lab-on-a-chip device contains all the integrated elements required for detecting the presence of e.g., viral or bacterial DNA in a biological sample and assessing the risk of disease. The present invention thus contemplates that both quantitative and qualitative measurements of DNA can be used to assess the subject's risk of having a disease or condition. For example, the presence of a Bacillus anthracis DNA in a test sample indicates the subject has been exposed to the bacterium which causes anthrax and may be at risk for having the disease associated therewith. Conversely, the absence of Bacillus anthracis DNA in a test sample indicates that the subject does not have the disease associated therewith.

Any number of infectious bacterial or viral diseases now known or later-identified can be rapidly detected in a test sample in accordance with the present invention. Such diseases detectable in accordance with the present invention include, but are not limited to: anthrax, small pox, Legionnaire's disease, AIDS, Hepatitis A, B, and C, tuberculosis plague, and malaria. In another aspect, the present invention permits the detection of cancer, leukemia, thalassemia, asthma, allergies, strep or sore throat, food poisoning, nearsightedness in children and adults, Nipah and sexually transmitted diseases.

The present invention also permits the detection of pharmaceuticals in a test sample. This aspect of the present invention can be used for e.g. rapid drug screening or for determining the presence of a drug in a particular tissue, for drug efficacy assessments, for example. Still another aspect of the present invention provides for the detection of genetically-modified food and for genetic fingerprinting. For example, in applications pertaining to genetically modified food, the chip will detect the artificially introduced genes in the food by PCR. For applications pertaining to the genetic fingerprinting, the chip will analyze DNA sequence variation between individual (human, plants, and animals) by PCR.

The chip apparatus and fluidic network can be manufactured at the micro scale level by existing microfabrication techniques such as glass etching, plastic hot embossing, plastic injection molding, resin casting, laser ablation, stereolithography photolithography, LIGA processes, CNC machining photocuring or metal forming techniques to form a chip with open structures such as open channels and assay stations. The open channels and assay stations can then sealed and closed with cover film or plate.

The dimensions of the channels can range typically from 1 micro meter to 10 mm. Therefore, microfabrication is only an option, not the exclusive means by which to produce the chip 100. Other more common technologies such as computer numerically controlled (CNC) machining, metal forming, plastic injection molding, or hot embossing can also be used for fabrication.

DETAILED DESCRIPTION OF THE FIGURES

In FIG. 1 and FIG. 2, exemplary microstructures of a chip apparatus 100 having a sample fluid preparatory area shown as constructed on substrate 36. Substrate 36 can be made of a suitable material such as glass, plastic, an elastomer such as poly-dimethylsiloxane (PDMS), metal, ceramic or a composite. To provide channels and assay stations, for example, various standard glass chemical etching techniques can be used on a glass substrate. If utilizing plastic (with or without metallic powder filling) to provide substrate 36, hot embossing with an embossing die, plastic injection molding, resin casting, laser ablation, stereolithography photolithography, LIGA processes, as known in the art, CNC machining photocuring and plastic chemical etching techniques can be used. LIGA processes typically comprise synchrotron radiation in a resist structure, such as polymethylmethacrylate (PMMA), and exposing the structure and chemically developing the structure to provide a micro mold based upon pattern of the resist structure. Metallic powder filling may be utilized in order to provide for improved conduction of heat, for example, when substrate 36 is comprised of plastic. If utilizing an elastomer substrate, a replication (a type of elastomer casting on a solid microstructured die) and molding techniques can be used. Additionally, silicon and silicon-based compounds may be utilized to provide substrate 36. Then substrate 36 may be sealed with the sealing layer 40 (not shown in top view). If sealed, various configurations of sealing may be provided, such as sealing a portion of the assay stations 26 only, or sealing assay stations 26 in combination with assay station channels 24, 28 and/or first and/or second multipurpose channel 30 and 22, respectively. The sealing layer is normally a plastic film that seals the channels and assay station or plurality of assay stations, except chamber 6 and all the inlets and outlets, by a bonding process including, but limited to, thermal bonding, electrostatic bonding, adhesive bonding. The sealing layer 40 can also consist of other materials such as glass plate or plastic plate or an elastomer like polydimethylsiloxane (PDMS).

In particular embodiments, the sealing layer 40 may also be comprised of a selfhealing/sealing type of material such as rubbers, elastomers, gels and/or a valve/lid which may be opened via mechanical, and/or electrical, and/or magnetic, and/or chemical means that would allow for introduction of a syringe, for example, into covered assay station 26, to provide for the application of a particular assay reaction component, for example, into assay station 26. Upon removal of the syringe, the sealing layer will self seal. In particular embodiments however, a self-healing/sealing type of material may not be utilized.

Fabrication of the assay stations or portions thereof and the various channels need not be restricted to only one of either substrate 36 or sealing layer 40. For example, a portion of assay station structures can be formed on the substrate 36 or sealing layer 40, and a portion of channel structure can be made on the sealing layer or substrate. Following bonding of sealing layer 40 and the substrate 36, the particular portions of various elements provided upon/in the substrate 36 and sealing layer 40 are brought together in proper alignment to provide the complete channel or other structure.

Embodiments of the apparatus 100 may include at least one flow controlling element. Flow controlling elements include various valves, gates and restrictions that may be provided at virtually any part of the apparatus, including channels as well as points of communication, for example, according to a user's desire or need for regulating/controlling fluid flow.

Assay station 26 may comprise at least one component of any number or type/class of assay reaction, the at least one component including, but not limited to, nucleic acids, probes, primers, antibodies, cells, assaying salts, catalysts, reporters, quenchers, enzymes, proteins, peptides, drugs, small molecules and fluorophores, for example. Additional examples include a synthetic molecule(s) from a combinatorial library of molecules, a peptide library a nucleic acid library or aptamer library. The at least one component of the assay reaction may be disposed into at least one assay station 26 via a carrier. A short list of carriers includes, but is not limited to, aqueous solutions, solvents and gels. Air and/or a gas may also be considered as a carrier for the deposition of at least one component into said at least one assay station 26 (spray or ink jet deposition, for example). The particular carrier or carriers so utilized may be adapted to be driven off by evaporation, for example. Other methods to drive off a carrier, such as ovens, lamps, lasers, force air, etc., are well known to those in the art. The at least one component, such as probes and/or cells for example, may be bound to the internal surface of assay station 26 by covalent bonds and/or absorption.

In the instance that an amplification reaction, such as PCR, is to be run in the assay stations 26, before bonding of the sealing layer 40, a nucleic acid fragment to be amplified and/or primer or primers may be deposited into each assay station 26 on the substrate 36 manually or by a liquid dispensing robot. The assay station 26 is then dried to drive off the carrier of the reaction component before adding the sealing layer 40. In particular embodiments, the sealing layer may be added before the drying of assay station 26 and in some embodiments the station may not need to be dry. Other embodiments may have the sealing layer 40 added during the running of the assay. In the case where a self-healing/sealing layer is utilized, the probes/primers may be added after assay station 26 is filled with sample fluid 56.

The nucleic acid fragment to be amplified includes, but is not limited to DNA or RNA fragments, cDNA, nucleic acid primers and/or probes conventionally obtained by the skilled artisan using standard methods. For example, a DNA fragment useful in accordance with the invention can be pre-fabricated in a commercial DNA synthesizer. The assay stations may be air dried in accordance with the teachings of the present invention. Drying may be carried out at room temperature at ambient atmospheric pressure. Depending upon the number of assay stations, drying may take from about 10 minutes to about 5 hours. Preferably, the assay stations are dried in about two hours.

Preferably, both the substrate 36 and the sealing layer 40 have hydrophilic surfaces to enhance the liquid flow by capillary force. A typical hydrophilic substrate 36 is glass. A normally hydrophobic substance such as a plastic can be treated to transform the substance into a hydrophilic substance by treating the plastic with diluted hydrofluoric acid or sulfuric acid. Another way to alter the surface properties of a hydrophobic substance, contemplated by the invention, is by adding a hydrophilic polymer solution, or by adding a surfactant to the hydrophobic substance, e.g., plastic.

For example, those of skill in the art are familiar with many various methods for treating/modifying surfaces, particularly surfaces that are to be utilized for microfluidic applications, such as plasma treatments or coatings, for example. As an example, glass, which is typically characterized as having hydrophilic surfaces, may be treated so that the surface or portions of its surface has instead hydrophobic characteristics. Such treatments may be utilized to provide apparatus and/or portions of the apparatus 100 having particular characteristics (such as wetting characteristics, for example) in accordance with the teachings of the present invention, in order to provide an apparatus configured according to a particular user's preference. The surfaces of the various channels and stations, for example, may have various portions (i.e. substrate, sealing layer) having either wholly, differentially or in any combination, treated surfaces in order to provide a desired arrangement of surface characteristics.

Channels such as 22, 20 and 30 in FIG. 1 for example, may be chemically etched by hydrofluoric (HF) acid on a glass slide for example, after patterning by photolithography using designed masks having desired patterns. Initially, etched slides are immersed into a freshly prepared mixture of about 70% sulfuric acid and about 30% aqueous solution of hydrogen peroxide (about 30% $H_2O_2$) at about 100° C. for about 10 min. The slides are then rinsed thoroughly by running tap water over them several times followed by deionised water, respectively. During this step, the slide is checked for total wetting achieved on every part of the slide, for example, and that there are no remaining hydrophobic patches. Of course, a portion or portions of the slide may not be treated if a user desires not to alter the surface characteristics at those area/areas. In the above example, hydrophilic glass surfaces are obtained.

In an exemplary method to obtain hydrophilic surface on plastic substrates, for example, poly(methyl methyacrylate) (PMMA), polycarbonate, polyimide, polypropylene, polyethylene etc, hydrophilic materials can be used to treat the plastic surfaces. The hydrophilic materials include poly (ethylene imine) (PEI), poly(vinyl alcohol), polyacrylate etc as known in the art. By coating or brushing a PEI solution, for example, and then drying in an oven for 0.5 to 1 hour, the previously hydrophobic plastic substrates are now provided with hydrophilic surfaces To obtain hydrophobic surface in channel 22 and a part of channel 24, the following steps are used.

Once treated, clean slides are stored in deionized water until ready for use. Before using, they are typically dried in an oven at about 100° C. at atmosphere pressure for about 1-2 hrs. If and when some precursor chemicals are used, the dried and cleansed material surfaces are further radiated by $UV-O_3$ oxidation for about 1 hr to remove the last traces of contaminants and improve self assembled monolayers (SAMs) quality. Precursor molecules (such as long alkyl trichlorosilanes, such as octadecyltrichlorosilane (OTS), for example) are prepared freshly at the ratio of about 10% concentration in a suitable solvent, e.g. Hexane, Hexadecane etc. These are then brushed or sprayed into the certain assigned regions for curing for about 15-20 min at room temperature, for example. When using fluorochemical acrylate polymer, such as EGC-1700 made by 3M, the coating solution is prepared freshly with about a 1.5% acetic acid and it is necessary for the finishing coated slides to be cured at an oven at about 80 to about 100° C. for about 30 min. Thus patterned hydrophilic (glass) and hydrophobic surfaces (treated glass) are provided. This is only one of many exemplary methods known to those of ordinary skill in the art for altering surface characteristics of a substrate.

Test sample inlet 2 for test sample (e.g. whole blood) is connected typically perpendicular to the upper surface of substrate 36 such that test sample inlet 2 is fluidically coupled to sample preparation chamber 6 through channel 5. Buffer inlet 4 is also connected typically perpendicular to the upper surface of substrate 36, and such that buffer inlet 4 is fluidically coupled to sample preparation chamber 6 through channel 7. Sample preparation chamber 6 is sealed at least partially on its lower surface by sintered glass block 31, to which absorbent 5 and/or a vacuum suction means such as a vacuum pump is applied to extract a mixture of e.g. whole blood sample, lysing buffer and washing buffer through the sintered glass block 31.

The block of sintered glass powder 31, which is inserted into sample preparation chamber 6, is also called porous glass. The typical size of a pore ranges from about 1 micro meter to about 500 micro meter. The sintered glass block 31 occupies the lower portion of the sample preparation chamber 6 and typically is rigidly fixed inside the chamber 6 by a slight size difference; that is, the size of the glass block 31 is slightly larger than the size of the sample preparation chamber 6. An adhesive substance can also be used to fix the glass block 31 inside the sample preparation chamber 6.

A vacuum, or liquid absorption by the absorbent 5, is created underneath the glass block 31 thereby extracting the sample, washing buffer and lysing buffer through the glass block 31. Elution buffer is injected into sample preparation chamber 6. Elution buffer penetrates into the glass block 31 and releases the DNA molecules from the surface of the glass block 31. Then, the DNA molecules diffuse (or by flow circulation) into the elution buffer contained in sample preparation chamber 6. So, therefore, the elution buffer contains DNA molecules at this time. Also, other chemicals required to perform the subsequent PCR reaction and fluorescent detection of the PCR product can be added to the elution buffer at this time.

In another embodiment, there is no need for the use of or addition of a lysing buffer to lyse cells. Instead, the cells are lysed utilizing heat. The cells may be heated to a lysing temperature either when still in sample preparation chamber 6 or may be conducted into the assay stations and lysed there. In a particular embodiment, a miniature heater and temperature sensor may be embedded into each assay station 26 in order to perform individual thermal cycling at each assay chamber 26. Furthermore, heat may be also utilized to evaporate an amount of elution buffer in order to increase the concentration of a solute, for example DNA, in a sample fluid. This evaporative step may be conducted at the sample preparation area 78 or at individual assay stations 26, for example, wherein the sealing layer 40, may be gas permeable but not liquid permeable, for example.

In another embodiment, various electrochemical sensors and electrical and electronic sensors may be embedded into each assay station 26. Utilizing this embodiment, a user is provided electrochemical-based detection/data as a result of assays run within said assay station. The data may be in the form of changes of electrical conductance, resistance and other indicators typical to experiments utilizing electrochemical detection, as known to those in the art.

The apparatus and methods provided by the present invention are useful for a number of various assays/reactions. For example, all of the required enzymes, fluorescent dye, deoxyribonucleotide triphosphates dNTPs, detergents, and other chemicals and buffers can be added into sample preparation chamber 6 through buffer inlet 4. If required to enhance the elution efficiency, vibrating actuator 34 can be applied to oscillate, typically vertically, to press diaphragm 48, thereby agitating the elution buffer in the sample preparation chamber 6 to allow more DNA molecules to leave the glass block 31 and enter the elution buffer which occupies sample preparation chamber 6.

A fluid, for example a gas or an oil, may be injected into sample preparation chamber 6 through either through test sample inlet 2 exclusively with buffer inlet 4 closed, or alternatively through test sample inlet 2 with buffer inlet 4 remaining open to act as vent until it is filled with elution buffer. The fluid purges the elution buffer containing the released DNA molecules, and causes exemplary flow controlling element, hydrophobic valve 8, to open, permitting elution buffer to enter into initially empty chamber for mixing sample solution and flow promoting fluid, where the elution buffer fills chamber 12. The valve 8 can also be a valve type that is operated by various other means such as mechanical, electrical, pneumatic or magnetic. At this time, the elution buffer is prevented from exiting the chamber 12 by hydrophobic valve 18 that is located at the entrance to main liquid distribution channel 20. Providing fluid can be achieved again through conventional techniques such as pressurization.

Before the buffer in chamber 12 flows out to assay stations, chamber 12 can also be used for the following purposes: (1) to meter the buffer flowing out of chamber 12 (that is, to control the volume of buffer flowing out of chamber 12 by proper choice of volume of chamber 12); (2) to retain buffer for period of time to let the DNA distribution homogenize before the buffer flows out of chamber 12; and (3) to increase DNA concentration, as mentioned previously, in the chamber 12 by evaporating a portion of the water in buffer. The resulting higher concentration of DNA in buffer flowing to assay stations 26 increases the DNA detection sensitivity and specificity.

In one embodiment, chamber 16 is provided for the introduction of flow promoting fluid (FPF), released through diffusion channels 14 to chamber 12. Suitable flow promoting chemicals include, but are not limited to, heparin, sodium dodecyl sulfate (SDS), cetyltrimethyl bromide (CTAB), Triton-X, Tween 20, NP-40 and any other surfactant that does not inhibit subsequent DNA amplification and detection chemistry, and does not fluoresce under detection light excitation. Upon diffusion of FPF into chamber 12, a concentration gradient of may be established in chamber 12.

In particular embodiments, one or more main sample fluid channel 20 is fluidically coupled to at least one first multipurpose channel 30 which is in communication with at least one first assay station channel 28, and at least one assay station 26. As the chemical concentration of FPF in the DNA containing sample fluid reaches a critical level, liquid wetting of the sample fluid over the surface of hydrophobic valve 18 becomes large enough to cause the buffer to flow through the valve 18 from chamber 12 into main sample fluid channel and further flow into first multi-purpose channel 30, first assay station channel 28, and assay stations 26. In this embodiment, the flow is caused by capillary pressure generated by surface tension which moves the liquid forward. Such surface tension is generated at the contact region between the sample fluid and the solid surface of the chip (that is, the surface of channels 20, 30, 28, and assay stations 26). With the addition of the FPF, the surface tension is lowered enough to cause the sample fluid to flow through valve 18 and move further into all other channels and assay stations.

During this capillary pressure flow, the air volumes in channels 20, 30, 28 and assay stations 26 are at least purged by sample fluid through at least one second assay channel 24, which are fluidically coupled to the assay stations 26 and second multi-purpose channels 22, so that channels 20, 30, 28 and assay stations 26 become filled with the sample fluid. To ensure that all of the assay stations 26 become filled with the sample fluid, the volume capacity of chamber 12 is designed to be at least equal to or greater than the combined volume of the channels 20, 30, 28 and assay stations 26.

To prevent the sample fluid from flowing into second multi-purpose channel 22, the following measures can be used: (1) Valves can be installed inside the second assay channel 24. Such valves can be actuated by actuating means such as mechanical, pneumatic or electromagnetic; (2) a porous material can be installed inside at least one second assay channel 24 to block the flow of sample fluid but allow air to vent into second multi-purpose channel 22; (3) a layer of hydrophobic material may coat at least a portion of the second assay channel 24 to block the flow of sample fluid but allow air to vent into second multi-purpose channel 22; the hydrophobic material typically can include, but is not limited to, poly (styrene-butadiene-styrene) (SBS), poly (methyl methyacrylate) (PMMA), polycarbonate, polyimide, polypropylene, OTS, fluorochemical acrylate polymer (such as EGC-1700 made by 3M) or epoxy resin. For example, SBS can be dissolved in an organic solvent to form a solution, which can be cast onto a glass or plastic surface to obtain a very thin film by drying. Epoxy resin can be directly dropped onto glass or plastic surfaces to form a thin film by ultra-violet (UV) curing or heating; (4) The hydrophobic material coats at least one second multi-purpose channel 22 so that the sample fluid can occupy second assay channel 24 but cannot enter into second multi-purpose channel 22 while air can be purged into second multi-purpose channel 22.

Figure 17:
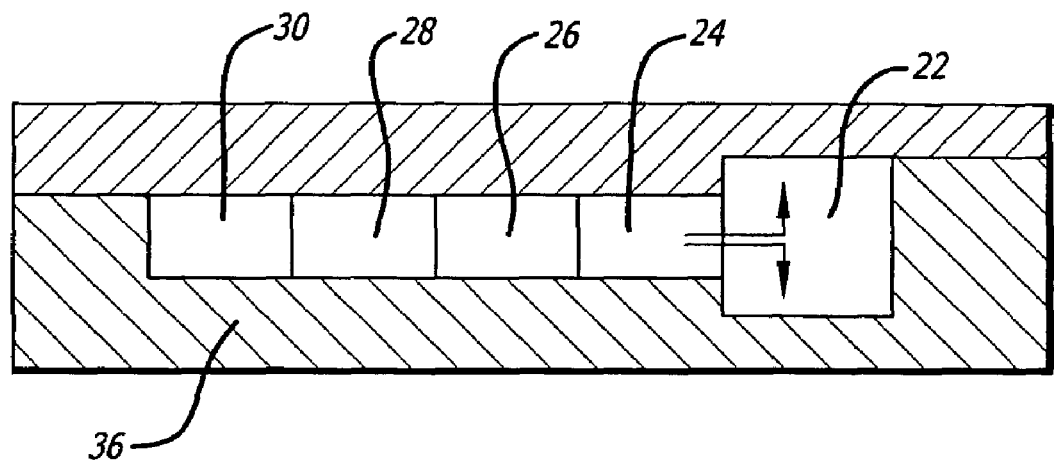
FIG. 17 is a side cross-sectional view of an exemplary configuration of channels in accordance with the teachings of the invention.

In particular embodiments, in order to stop sample fluid 56 flow from entering second multipurpose channel 22, the width/diameter of second multipurpose channel 22 is provided to be larger that the width/diameter of second assay channel 24 as depicted in exemplary FIG. 17, which depicts a side cross-sectional view of an example of this type of configuration. A drastic enlargement, which may be sharply made, at approximately the end of assay channel 24 is effective to stop the flow of sample fluid 56 and prevent it from entering second multipurpose channel 22. Line depicted between the various channels are only for illustrative purposes, to show graphically the various channels and their spatial relationships in the exemplified figure.

When using octadecyltrichlorosilane (OTS), itis preferably prepared freshly at the ratio of about 10% concentration in a suitable solvent, e.g. Hexane, Hexadecane etc. Following this, the solution is then brushed or sprayed into the certain assigned regions for curing for about 15-20 min at room temperature, for example. In this way, hydrophobic surfaces are obtained. When using fluorochemical acrylate polymer such as EGC-1700 made by 3M, the coating solution is prepared freshly with about 1.5% acetic acid and the finished coated slides are preferably cured in an oven, for example, at about 80 to about 100° C. for about 30 min.

Digital camera 32 detects when all the assay stations 26 are filled by sample fluid. The digital camera may be a camera with a charge-coupled device (CCD) sensing element and all possible types of suitable optics for acquiring images. An optical filter is positioned in front of the sensing element of the camera, so that only light of specific wavelengths emitted from the liquid in assay stations 26 is allowed to pass through the filter and reach the sensing element (to be detected by the camera).

At the time that all the assay stations 26 are filled, isolation medium 54 may be introduced through selected combinations of inlets 42, 44, 46, and 21, for example, which are fluidically coupled to first and second multi-purpose channel 30 and 22 respectively, for example, by any of the following non-comprehensive list of means: electro-osmosis pumping, positive pressurization (such as injection with a syringe), capillary flow, electrowetting, thermocapillary flow and/or vacuum suction. In embodiments where a sealing layer 40 is not provided over the multipurpose channels, isolation medium may be deposited by casting and/or robotic dispensing, for example, which would purge sample fluid 56 from the first multipurpose channel 30. Filling channels 30 and 22 with isolation medium can be executed sequentially or simultaneously, and is typically performed by the introduction of isolation medium through inlets that first purge sample fluid from the first multi-purpose channel and then subsequently isolation medium is introduced into the second multi-purpose channel to purge air therefrom.

Therefore, the isolation medium 54 fully fills first and second multi-purpose channels 30 and 22. The isolation medium 54 is selected so as to be impermeable to the elution buffer, i.e. the buffer cannot diffuse into medium 54. The isolation medium 54 typically can be wax, heat cured wax, oil, phase-changing plastics, thermally curable polymer liquid, cyanoacrylate and its derivatives, two-part epoxies or ultra-violet (UV) or visible light curable polymer liquid and hot-melt materials (such as those typically utilized in glue guns, for example). Further exemplary isolation mediums 54 include, but are not limited to, thermally cured polymer, such as polydimethylsiloxane (PDMS) elastomer, as well as other silicone elastomer and liquid silicone precursors. Curing activation temperatures may be higher than about 40 degrees C.

Exemplary ultra-violet (UV) curable isolation medium 54 such as polyacrylate and its derivatives, polyurethane precursors and its derivatives may also be utilized. The UV or other appropriate radiation sources include a UV lamp that is focused onto multipurpose channel 22 and/or 30, for example, by a lens or lenses, a UV lamp illuminating onto multipurpose channel 22 and/or 30 areas that remain exposed after application of a mask having appropriate cut-out portions which provide multipurpose channel 22 and/or 30 areas exposed to UV, for example. Additionally, a localized irradiation source that may be directed onto isolation-medium 54 containing multipurpose channels 22 and/or 30 may also include a localized UV source such as fiber optics.

Additional exemplary isolation medium 54 may also comprise any adhesive which solidifies as a result of solvent evaporation, for example. When utilizing such isolation medium 54, provisions, such as appropriate venting holes and/or slots, in sealing layer 40 and/or substrate may be provided. The venting holes and/or slots may be provided in sealing layer 40 areas that cover the multipurpose channels, for example.

Isolation medium 54 is preferably, substantially immiscible with water and/or aqueous fluid, including with water and/or aqueous fluid containing a surfactant. Isolation medium 54 may be non-transparent and/or fluoresce (not at a wavelength or intensity that may interfere with the assay) and have low viscosity.

In embodiments wherein isolation medium 54 remains in liquid form after introduction and filling of the multipurpose channels 22/30, for example, a solidifiable sealant 67 (for example, wax, hot melt adhesive liquid, polymer liquid, elastomers) are to be deposited to and seal all of the interfaces between the ambient atmosphere and fluids (such as sample fluid 56 and/or isolation medium 54) in multipurpose channels 22 and 30. Other sealing structures, such as caps, lids and valves, can also be utilized to seal off air-liquid interfaces and it is preferable that solidifiable sealant 67 and the caps, lids, and valves can endure temperatures up to and around 100° C. The sealant 67 and/or the other sealing structures form a fixed volume of liquid/fluid in the assay stations and suppresses the generation of vapor and during PCR, for example, and any other ration that takes place at elevated temperatures. The solidifiable sealant 67 may be deposited via robotic, manual and other dispensing means, as known in the microfluidic arts.

In still other embodiments, the multipurpose channels may have, instead of oil/wax-like-type isolation medium 54, ambient air or saturated humid air, or any other humidity saturated vapor, introduced and disposed therein after conduction of sample fluid 56 into the assay stations, to minimize evaporation from assay stations. Ambient air or saturated humid air, or any other humidity saturated vapor may be utilized to purge sample fluid 56 from first multipurpose channel 30.

Additionally and in further embodiments, the chip 100 may be subjected to pressure above atmospheric pressure when placed inside an enclosure 514, such as a molecular analyzer, during analysis such that the evaporative temperature of sample fluid 56 is raised in order to minimize sample fluid evaporation from assays stations.

In this embodiment the DNA or other chemicals in the sample fluid contained in each assay station 26 are isolated within the domain of the assay stations 26 and the first assay station channel 28 and second assay channel 24 so that the DNA or other chemicals do not diffuse to an adjacent assay station in the assay station array. The isolation property of the isolation medium 54 is sustained at temperatures up to and around 100° C. Since the highest temperature for the PCR process is 95° C., no cross contamination occurs in the subsequent DNA amplification step. The injection of the isolation medium 54 can be achieved through conventional techniques such as electro-osmosis, positive pressurization by injection, capillary flow electrowetting, thermocapillary flow or vacuum suction.

Additionally, a washing step may be added in order to wash away at least one undesired component of a reaction, such as non-specific binding of a labeled probe or other unwanted reaction components, for example, in assay stations 26. This may be utilized in embodiments wherein a probe/marker molecules are utilized which are strongly bound to the internal surface of assay station 26, for example, and also bind to the particular molecule (DNA, for example) that is of interest. Upon the completion of the assay reaction, a washing step, comprised of introducing a washing buffer (via vacuum or pressure, for example) into the multipurpose channels and assay station and channels, is provided in order to wash away nonspecific components of the assay reaction. The markers/probes that are bound to assay chamber 26 surfaces remain behind and are then assayed for the presence or absence of the molecule of interest bound to the marker/probe.

Each assay station 26 may contain a fluorescent dye. Digital camera 32 captures both white light and/or the fluorescent emission images from fluorescent dye. In the case where the chambers, channels, and assay stations, i.e., fluid compartments and channels, are not embedded underneath the surface of the substrate 36, and are otherwise exposed to the environment, a sealing layer 40 may be applied to the upper surfaces of all of the fluid compartments and channels 20, 30, 28 and assay stations 26. The sealing layer 40 should be bonded to the substrate 36 preferably before the test sample is added to the sample preparation chamber 6. The sealing layer 40 may not applied to sample preparation chamber 6, and the mouths of the inlets 2, 4 and 21, 42, 44, 46. The sealing layer 40 can be omitted from the upper surface of channels 24 and/or 22 depending upon the particular assay protocol utilized and the temperatures associated therewith. Sealing layer 40 may in particular embodiments seal off the channels and assay stations from the environment, enhance the capillary flow, and enable the liquid flow by injection or vacuum. The sealing layer 40 is normally a plastic film that seals the channels and assay stations, except sample preparation chamber 6 and all the introduction inlets, by a bonding process including, but limited to, thermal bonding, electrostatic bonding, mechanical jointing and adhesive bonding. The sealing layer can also be comprised of at least one of a glass plate, a plastic plate, a thermoplastic, an elastomer, a plastic film and a thermally activated adhesive. Additionally, sealing layer may be comprised of the same material as the substrate. Preferably, sealing layer 40 and substrate 36 are transparent to UV and other wavelengths, including those in the visible spectrum, and do not generate fluorescence that will interfere with experimental measurements/results.

In additional embodiments, sealing layer 40 may also be provided with holes/vents that are located at a variety of locations. For example, at least one hole in the sealing layer may be provided at a location, or locations in the case of a plurality of holes, over the various areas, such as channels or waste reservoir 45, for example. Furthermore, it is also contemplated that sealing layer 40 may be comprised of a material that is gas permeable. This would allow venting fluids to escape, for example, while providing a barrier to the loss of a liquid fluid from the apparatus 100, for example. If such a sealing layer is provided, venting holes may not be required to allow fluids and various mediums to flow through the various channels.

The channels 20, 30, 28, 24 and 22 can range in width typically from about 1 micro meter to about 5 mm, while the channels can range in depth typically from about 1 micro meter to about 1 mm. The assay stations 26 can range in width or diameter typically from about 1 micro meter to about 10 mm, and typically from about 1 micro meter to about 1 mm in depth. The surface wetting properties and dimensions of each type of channel 20, 30, 28, 24 and 22 can vary from the other types of channels. All of the structures can be manufactured using such processes as micro electro-mechanical systems (MEMS) technology, computer numerically controlled (CNC) machining, laser machining, electrical discharge machining (EDM), chemical etching, injection molding, hot embossing, or stamping.

Each assay station 26 may subject to a thermal condition required for DNA amplification as previously discussed. Such thermal conditions include thermal cycling required for the polymerase chain reaction (PCR).

Moreover, in an alternate embodiment of the present invention, the FPF can also be added through test sample inlet 2 or buffer inlet 4 to elution buffer in sample preparation chamber 6 to actuate the flow into the assay stations 26. In this case, there is no need for chamber 12, channels 14 and chamber 16. This chip design is shown in FIG. 3 and FIG. 4. Here, the valve 8 assumes the function of valve 18 shown in FIG. 1 and FIG. 2. In all other respects, the design of the chip 100 and the operating method of sample preparation and analysis is identical to that presented for FIG. 1 and FIG. 2. Therefore, no additional discussion is presented.

Also, if the chip surface (surface of all the channels and all the assay stations) is hydrophilic, there is no need to use a FPF at all at any stage of chip operation. In this case, since the sample fluid is aqueous, it can flow into all the channels and assay stations by itself when valve 8 is opened. Both valve 8 and valve 18 can be operated by any means, for example mechanical, electrical, magnetic, chemical or pneumatic.

Figure 5A:
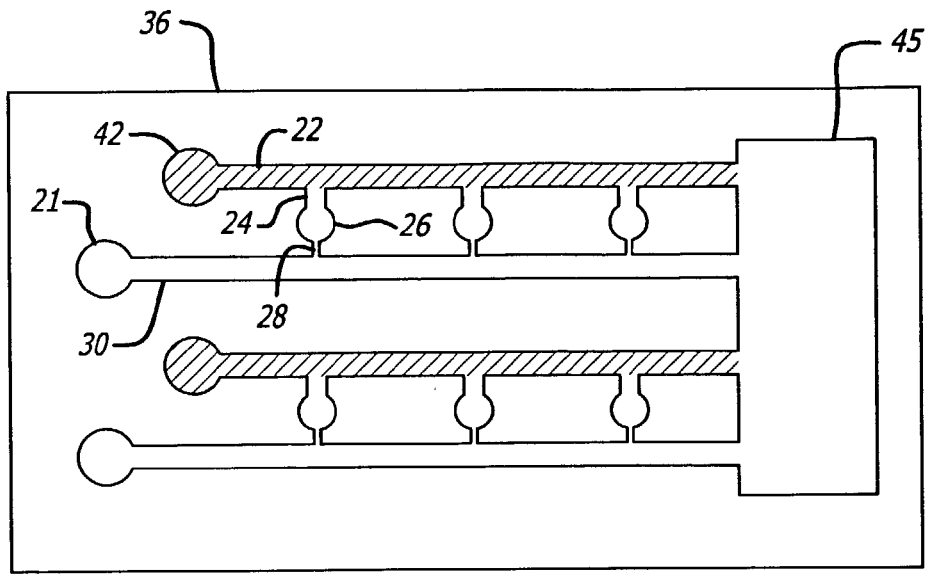
FIG. 5A is a plan view of an exemplary microfluidic chip in accordance with the teachings of the invention.

In particular embodiments, the apparatus may not be provided with a sample preparation area wherein preparation of sample fluid is conducted "off-chip". Exemplary configurations such as those depicted in FIGS. 5A-E may therefore be provided. In FIG. 5A substrate 36 has at least one assay station 26 having in communication thereto a first assay channel 28 and a second assay channel 24. Additionally, isolation media inlet 42 is provided in communication with second multipurpose channel 22. Furthermore, exemplary sample solution inlet 21 is also provided in communication with first multipurpose channel 30. In the embodiment of FIG. 5A, a reservoir 45 is depicted in communication with first 30 and second 22 multipurpose channel. While only two sets of assay stations, assay station channels and multipurpose channels are shown, any number of a plurality of sets may be provided. Additionally, sealing layer 40 may be provided over particular areas according to particular embodiments as described previously (not shown due to top view of FIGS. 5A-E). Exemplary configurations include sealing layer 40 covering assay stations 26 only or in combination with one or both multipurpose channels, for example, depending upon the type of assay to be run and the characteristics of fluids that will be utilized in conjunction with substrate 36.

In some embodiments, first assay channel 28 has a smaller cross-sectional area than the second assay channel 24, as shown in FIGS. 5A-E. This reduces the speed and/or flow of sample fluid 56, that enters assay station 26, thus allowing the air being displaced, via sample fluid 56 entry into assay chamber 26, to be conducted through second assay chamber channel 24 and into second multipurpose channel 22. This reduces the likelyhood that air pockets will form and be trapped within assay station 26 as sample fluid 56 flows into assay station 26 and eventually into assay station channel 24.

While first assay station channel 28 is depicted exemplarily herein as having a circular cross-sectional shape/profile, this channel may have any shape that provides flow restriction to minimize sample fluid 56 flow out into first multipurpose channel 30.

Figure 5B:
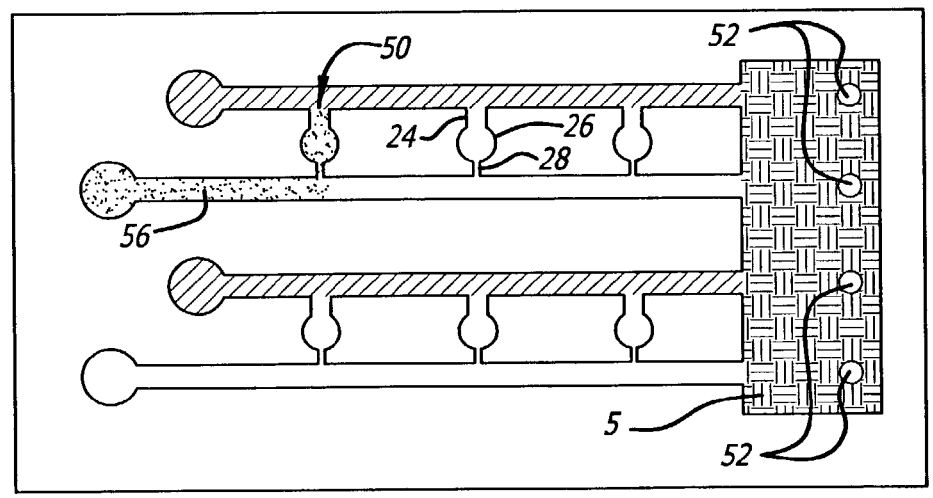
FIG. 5B is a plan view of an alternative exemplary microfluidic chip.

In FIG. 5B, a portion 50 of second assay station channel 24 adjacent second multipurpose channel 22, may be provided with surface characteristics that are non-conducive to the flow of sample solution 56. For example, second multipurpose channel 22 may have or be treated to provide a hydrophobic surface. In this embodiment, if sample solution 56 is an aqueous solution, the sample solution 56 will flow into assay station 26 via sample solution inlet 21, and first multi-purpose channel 30, which in this example has hydrophilic surface characteristics. Similarly, the surfaces of first assay channel 28 and assay station 26, also have hydrophilic surfaces, for example. Sample solution 56 flows to second multipurpose channel 22 and stops, due to second multipurpose channel's 22 hydrophobic surface characteristic or, as in particular embodiments as depicted in FIG. 17, the abrupt expansion of channel diameter from second assay channel 24 to second multipurpose channel 22. As depicted, portion 50 of second assay channel 24 may also have hydrophobic surface characteristics at which point sample fluid 56 flow would stop, shown in FIG. 5B, C, for example.

In the embodiments depicted in FIGS. 5B, C, reservoir 45 may be provided with absorbent 5. Absorbent 5 may be comprised of at least any one of cellulose-based material or synthetic material, polyacrylamide gels, particles and porous materials. Reservoir 45 may be sealed by sealing layer 40 or may be open to the atmosphere. Furthermore and in particular embodiments, when absorbent 5 may be covered by sealing layer 40, as shown in FIG. 5B (top view), vents 52 may be provided so that fluid flow in the various channels may occur. Additionally, while reservoir 45 and absorbent 5 are herein depicted as being of sufficient size to be in communication with a plurality of terminal portions of multipurpose channels, it is also contemplated that terminal portions of the multipurpose channels may be in communication with exclusive reservoirs and/or absorbent 5 not in communication with any other multipurpose channel.

In order to seal assay station 26, isolation medium 54 is allowed to flow into first multipurpose conduit 30. Isolation medium 54 may be introduced via various methods and in accordance with various embodiments of the instant invention. For example, isolation medium 54 may be introduced into first multipurpose channel 30 via isolation medium inlet 21. In particular embodiments, for example in FIGS. 5A-E as well as FIGS. 1 and 3, isolation medium inlet 21 may serve a dual or multipurpose as sample fluid inlet 21 and as an inlet for isolation medium as shown in FIG. 5A. In other embodiments for example, as also seen in FIG. 1, isolation medium 54 may be introduced via an inlet 42 or inlets that do not serve a dual purpose but rather are inlets to second multipurpose channel 22 that is conducive to the flow of air and an isolation medium 54. As previously discussed, isolation medium 54 not only serves to seal assay station 26, for example, but also provides for the displacement of sample fluid 56 from first multipurpose channel 30. The displaced sample fluid 56 may flow to a reservoir 45, as exemplified in FIG. 5A, which may or may not be sealed with sealing layer 40 and may or may not contain absorbent 5.

The displacement described so far results in the flow of sample fluid 56 out of first multipurpose channel 30. However, additional displacement may also take place by the application of isolation fluid 54 into the second multipurpose channel 22, wherein the isolation fluid 54 displaces not sample fluid 56, but air. Recall that in this embodiment the surface of second multi-purpose channel 22 may be inherently or treated to be hydrophobic, for example, and thus acts to halt the flow of sample fluid at area 50. Upon introduction of isolation medium 54 into the second multipurpose channels, the air therein is displaced and thus assay station 26, or pluralities thereof, are sealed by said isolation fluid 54. This addresses the concern of evaporation and cross contamination of the contents of one assay station with others.

Figure 5C:
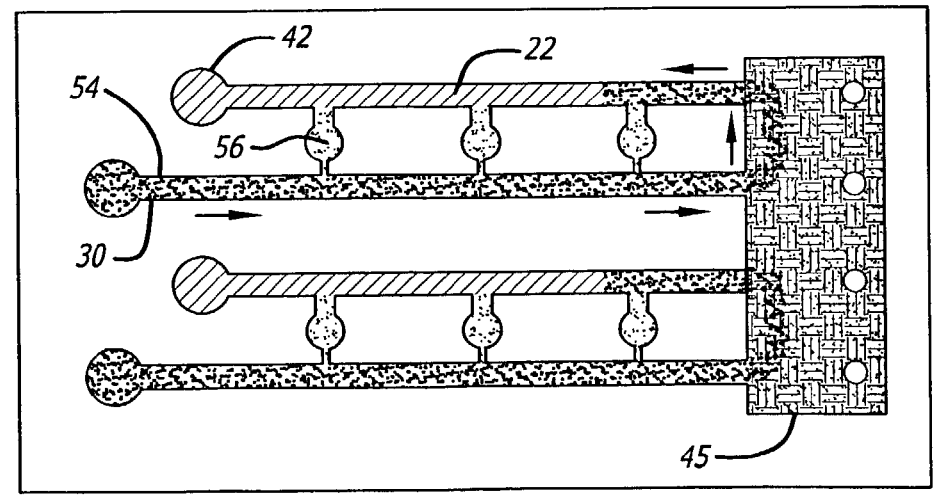
FIG. 5C is still another view of an exemplary microfluidic chip in accordance with the teachings of the present invention, having sample fluid and an isolation medium therein disposed.

There are a number of methods by which isolation medium 54 may be introduced to exemplary second multipurpose channel 22. According to the embodiment depicted in FIG. 5C, isolation medium 54 is introduced via inlet 21, flows and displaces sample fluid 56 from the first multipurpose channel into reservoir 45. This results in the partial sealing of assay station 26 at the lower hand portion, as depicted. Isolation fluid may then flow into absorbent 5 and then come into communication with second multipurpose channel 22, as indicated by the arrows, and flow into the second multipurpose channel 22, displacing the air therein and sealing the upper hand portion of assay station 26, resulting in the complete sealing of the assay station 26 or stations. In this embodiment, inlet 42 may act as a vent and not as a point of entry for the introduction of isolation fluid into second multipurpose channel 22, for example, as shown in FIG. 5D.

Figure 5D:
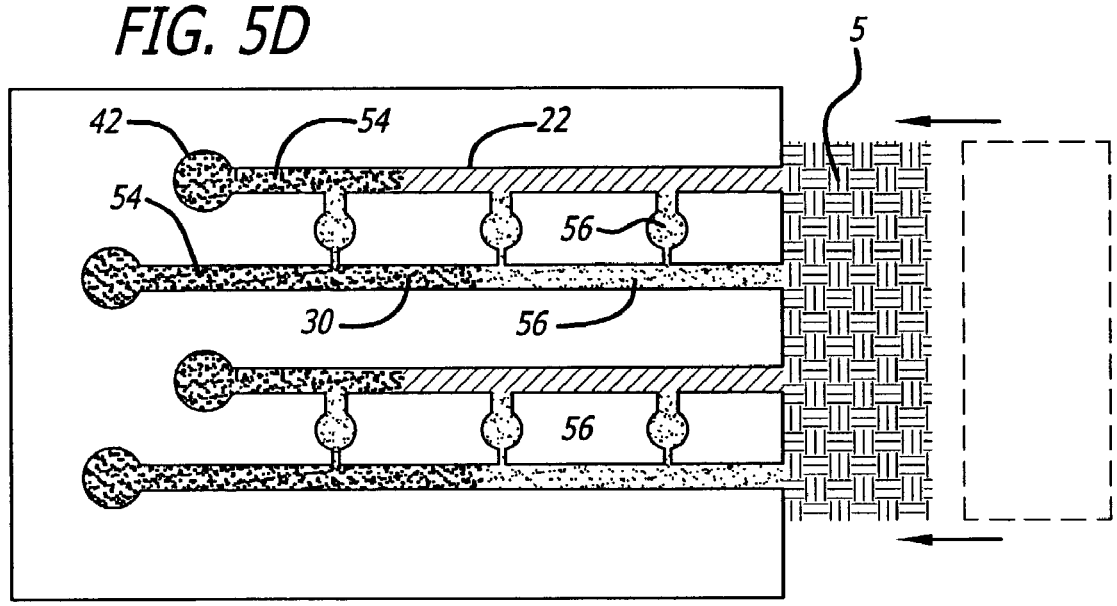
FIG. 5D is another embodiment of an exemplary microfluidic chip having sample fluid and isolation medium and a detachable absorbent.
Figure 5E:
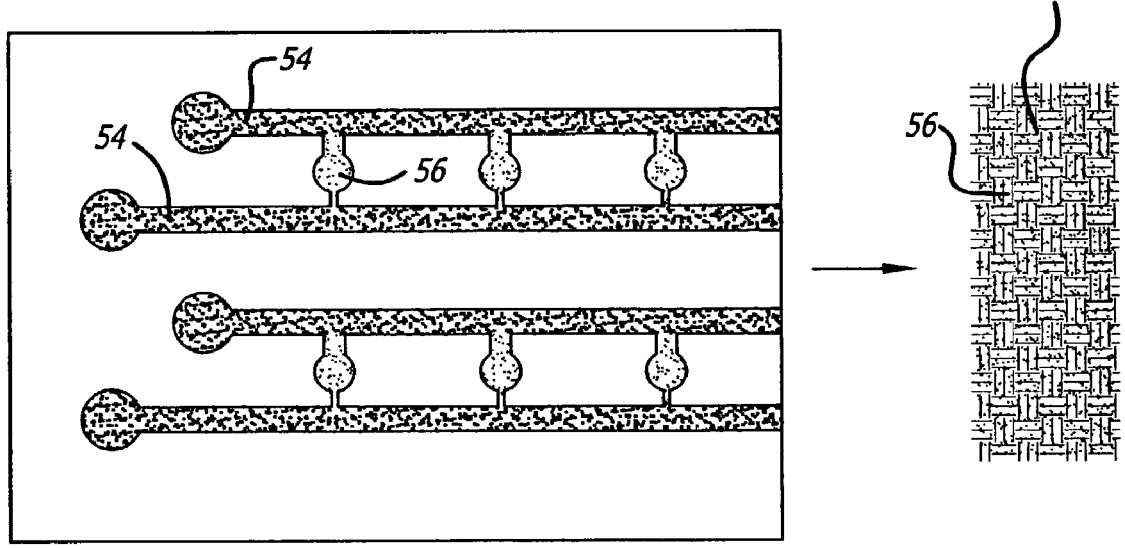
FIG. 5E depicts the chip of FIG. 5D having isolation medium therein disposed, sealing sample fluid in a plurality of assay stations and an absorbent having excess sample fluid removed.

FIG. 5D depicts a detachable absorbent 5 component, that may be bought into communication with the multipurpose channels. Here, the absorbent 5 provides for the uptake of excess sample fluid 56, and may also uptake excess isolation medium 54. Further, the application of absorbent 5 may also provide to speed up the filling of assay station 26 or stations by providing another "pulling" force onto the columns of sample fluid 56 in the respective first multipurpose channel. In FIG. 5D, isolation medium 54 has been introduced via inlets 21 and 42. In FIG. 5E the assay stations have been sealed and the absorbent 5 removed, now having excess sample fluid contained therein. At mentioned previously, absorbent 5 may also have absorbed therein isolation medium 54.

Figure 18:
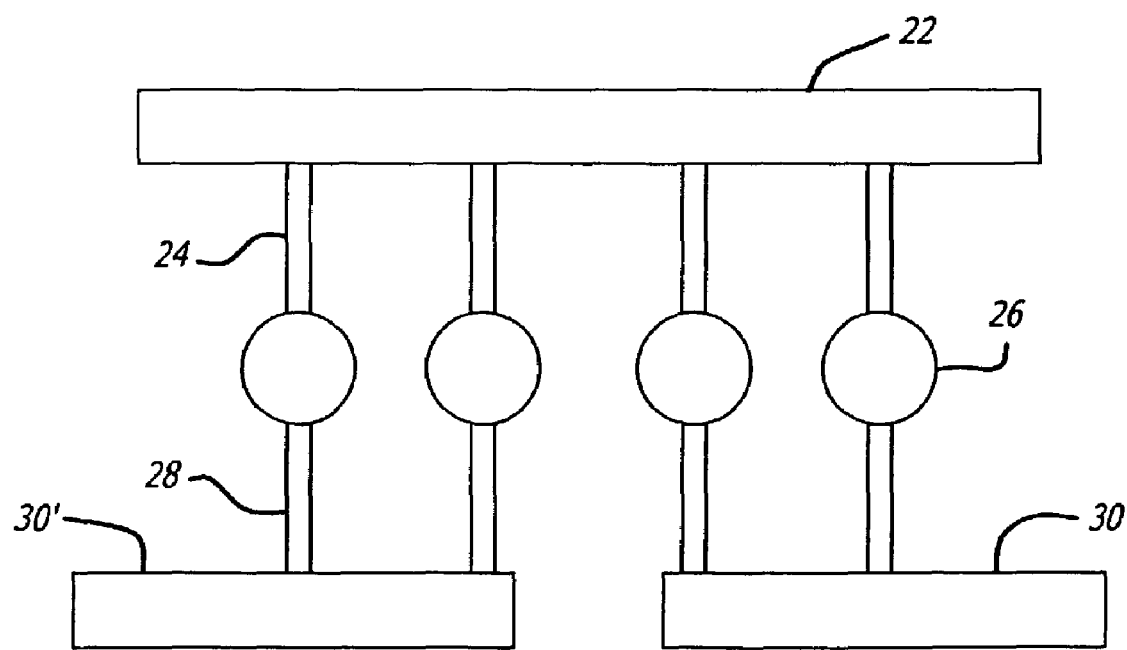
FIG. 18 is another exemplary embodiment of channels for multiple sample testing according to the teachings of the invention.

Alternative embodiments may provide for the introduction of multiple sample fluids 56 into the chip. An exemplary configuration is depicted in FIG. 18. Here a common second multipurpose channel 22 is provided in communication with multiple assay stations. The plurality of assay stations may be in communication with a plurality of separate first multipurpose channels, for example as shown (30 and 30'), into which sample fluid 56 which may differ from one another, may be introduced. This provides for assaying/ testing of multiple/different sample fluids on one apparatus.

FIGS. 6A-C depict an alternative embodiment. In this embodiment, assay station 26 or stations, are provided with a venting hole 66 formed in sealing layer 40 (not shown in FIG. 6A, a top view). This is shown more clearly in FIG. 6B, a side view of exemplary FIG. 6A. Here, assay station vent 66 is shown open to the atmosphere. Supports 62 are provided to support isolation medium platform 60 which is disposed over at least the assay station vent 66 and defines gap 64. As in previous embodiments, sample fluid 56 is introduced into first multipurpose channel 30 and flows and fills assay station 26 via first assay channel 28. Here, instead of flowing to a second multipurpose assay channel, sample fluid 56 fills assay station 26 (or stations) as well as assay station vent 66, as seen in FIG. 6B. Subsequently, isolation medium 54 displaces sample fluid 56 in first multipurpose channel as before. However, isolation medium 54 now is introduced to gap 64. Isolation medium 54 flows to fill in gap 64 defined by isolation medium platform 60 and sealing layer 40, as shown in progress in FIG. 6C. FIG. 6D depicts this filling and sealing process from a cross sectional side view of FIG. 6C. FIG. 6E depicts this exemplary embodiment at the point where the sample fluid in assay stations is sealed by isolation medium 54.

Figure 6F:
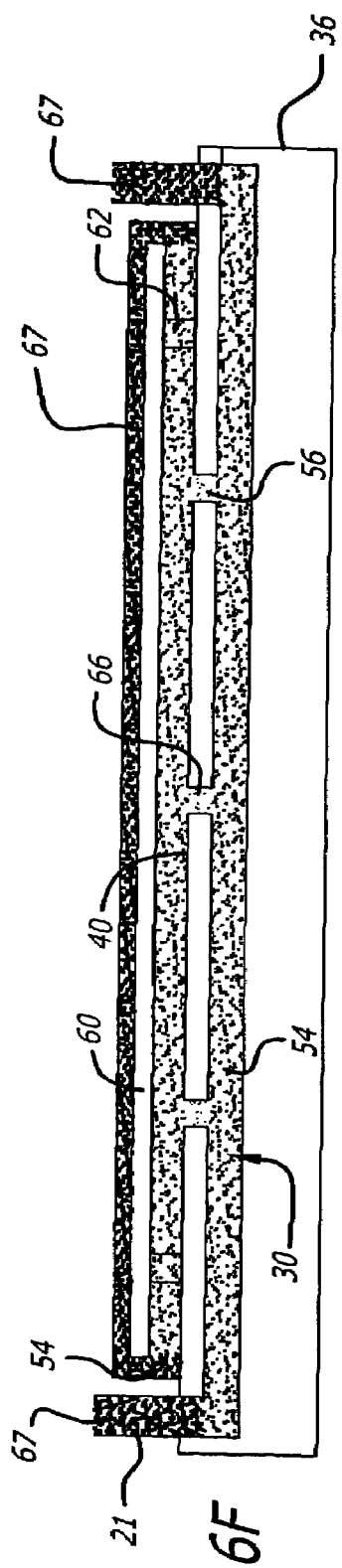
FIG. 6F shows another exemplary sealing arrangement in accordance with another aspect of the invention.

In embodiments where a non-solidifiable isolation medium 54 is utilized, and isolation medium 54 does not solidify, a solidifiable sealant 67 may be deposited all around isolation medium platform 60 and into all outlets and inlets 21, for example, in order to seal off and isolate all the fluidic paths (channels and inlets) from the atmosphere, as depicted in a side view in FIG. 6F. This thus forms a fixed volume (of sample fluid 56 and isolation medium 54, for example)of liquid inside the chip 100 to suppress vapor generation during PCR and other reaction at elevated temperature. Sealant 67 can be in form of wax, hot-melt compositions, adhesive liquid, polymer liquid and elastomer for example. Additionally, this solid sealant effect can also be achieved utilizing caps, lids and/or valves, in any preferred combination. It is preferred that solidifiable sealant 67 as well caps, lids and/or valves endure temperatures up to about 100° C.

Figure 6G:
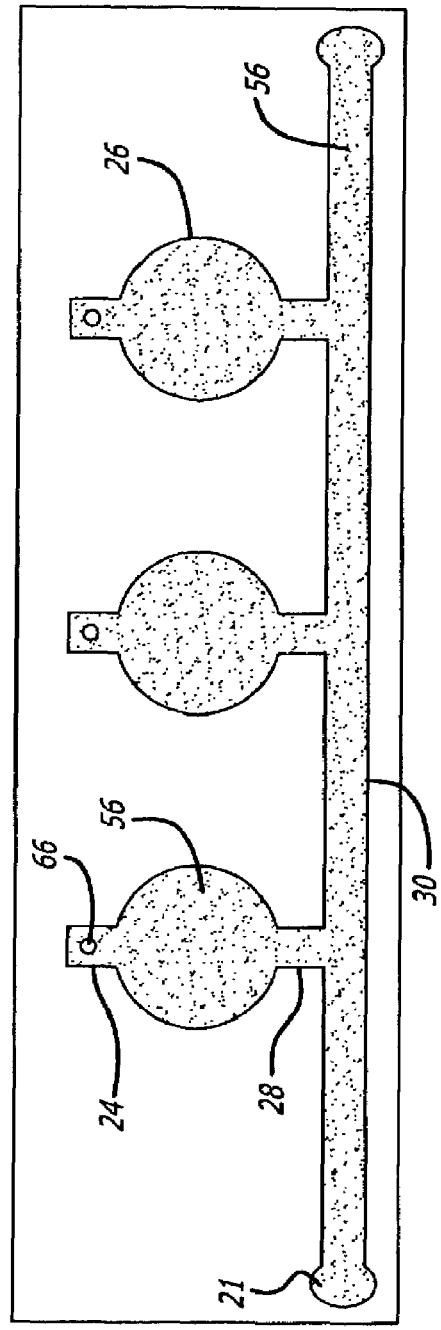
FIG. 6G depicts another exemplary microfluidic chip made in accordance +with the teachings of the invention.

Turning to FIG. 6G, another exemplary configuration is depicted. Here, isolation medium platform 60 is not utilized and assay station vent 66 has been moved to an exemplary position over assay station channel 24. In certain embodiments, solidifiable sealant 67 may be disposed directly onto sealing layer 40 (not shown in this top view) to cover assay station vent 66 as well as outlets and inlets 21, in order to isolate all the fluidic paths and provide a fixed volume of fluid, as detailed above, from the atmosphere and thus minimized and/or eliminates mixing of fluids (sample fluid 56 in assays stations, for example). In particular embodiments, the sequences of the filling of sample fluid 56 and isolation fluid 54 may reversed.

FIGS. 7A1-7C4 depict an exemplary sequence of filling events. In these examples, first multipurpose channel 30, first and second assay channel, 28 and 24, as well as assay station 26, have hydrophilic surface characteristics, while second multipurpose channel 22 has a hydrophobic surface. In particular embodiments, at least a portion of sealing layer 40 located above multipurpose channel 22 has a hydrophobic surface.

Figures 1, 7A:
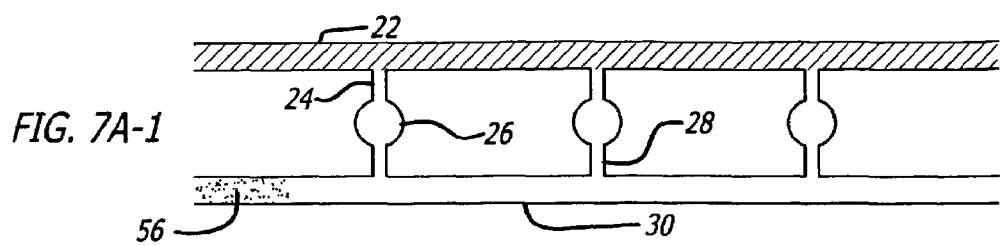
Figures 2, 7A:
Figures 3, 7A:
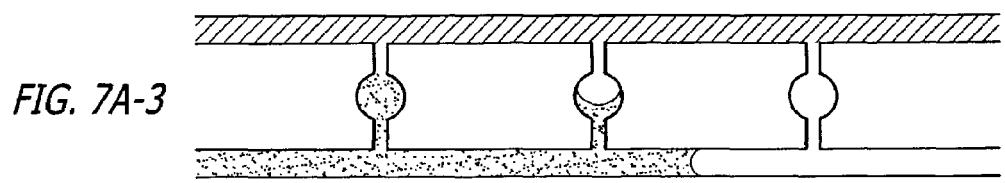
Figures 4, 7A:
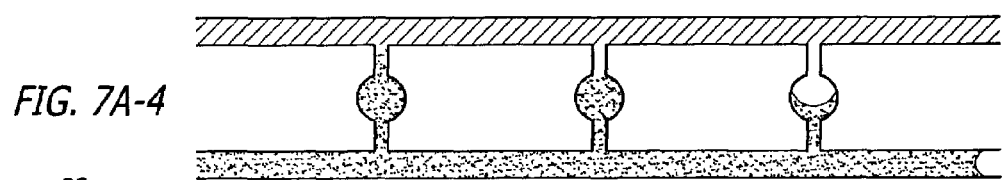
Figures 1, 7B:
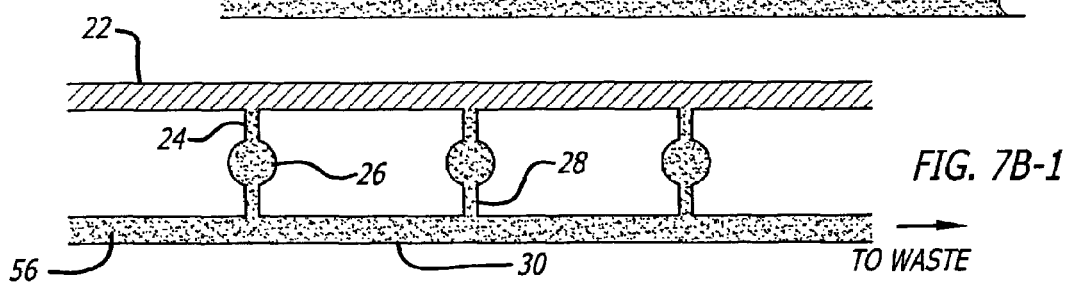
Figures 2, 7B:
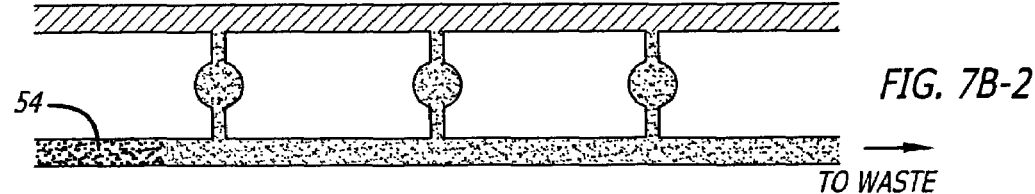
Figures 3, 7B:
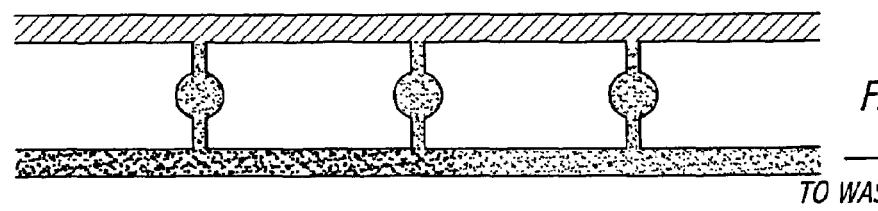
Figures 4, 7B:
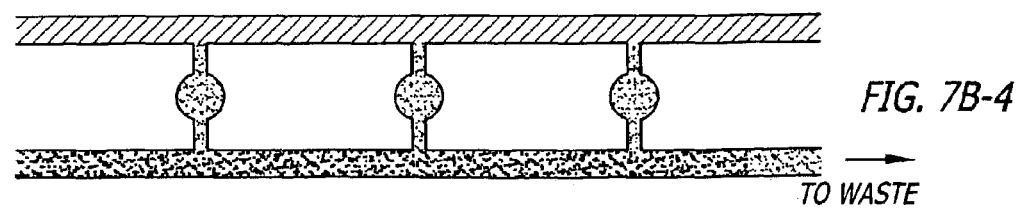

FIGS. 7A-1 to 7A-4 depict an exemplary flow and filling sequence wherein sample fluid 56, having been introduced into first multipurpose channel 30, flows through and fills the first multipurpose channel 30, first assay station channel 28 and assay station 26, and flows into the second assay station channel 24 and stops adjacent to the second multipurpose channel 22. Subsequently, as shown in FIG. 7B1 to 7B4, isolation fluid 54, having been introduced into the first multipurpose channel 30, displaces sample fluid 56 which does not flow into the second multipurpose channel 22 due to the differences in surface characteristics between second multipurpose channel 22 (in this example, hydrophobic) and the second assay station channel 24 (hydrophilic). This results in the isolation and partial sealing of the assay station 26 via the interface between the sample fluid 56 in the first assay station channel 28 and the isolation medium 54 in the first multipurpose channel 30.

In FIG. 7C1 to 7C4, isolation medium 54, having been introduced to second multipurpose channel 22, flows therethrough and displaces the air within. The flow of isolation medium 54 through second multipurpose channel 22 completes the sealing of the plurality of assay stations. As mentioned previously, isolation medium 54 and sample fluid 56 are substantially immiscible with one another, thus providing a seal at points where they meet, such as shown in FIGS. 7C-4, for example. In particular embodiments wherein isolation medium 54 does not solidify after introduction into multipurpose channels 22 and 30, for example, a solid seal may be utilized to seal the inlets/outlets of the multipurpose channels. Such a solid barrier prevents vapor generation or expansion of sample fluid 56 at higher temperatures.

Figure 2:
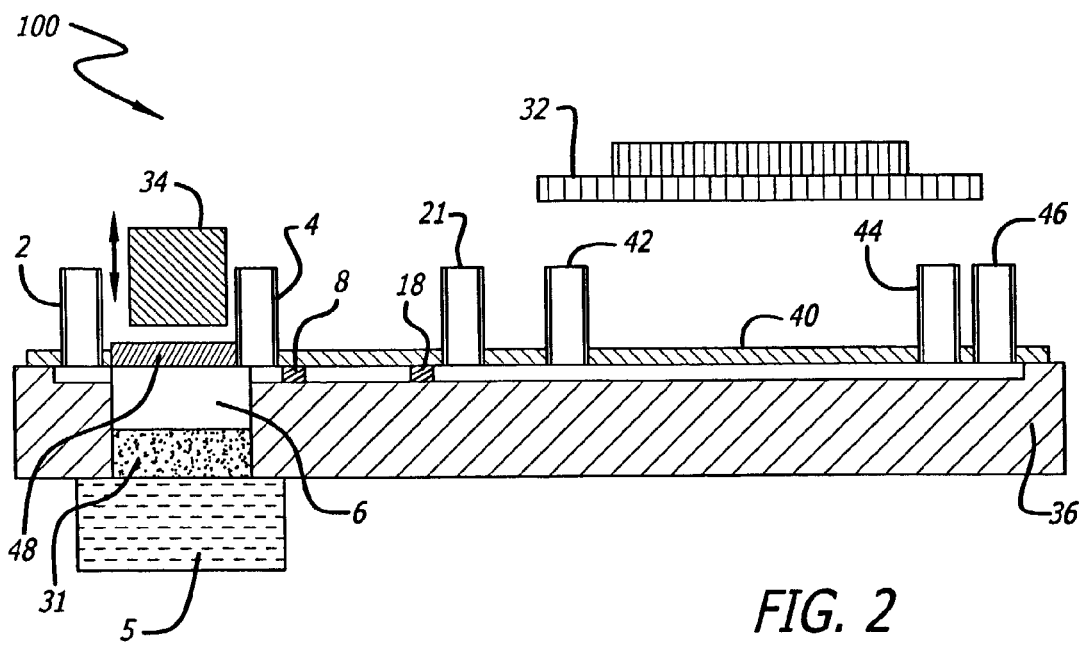
FIG. 2 is a side view of the exemplary chip of FIG. 1.
Figure 3:
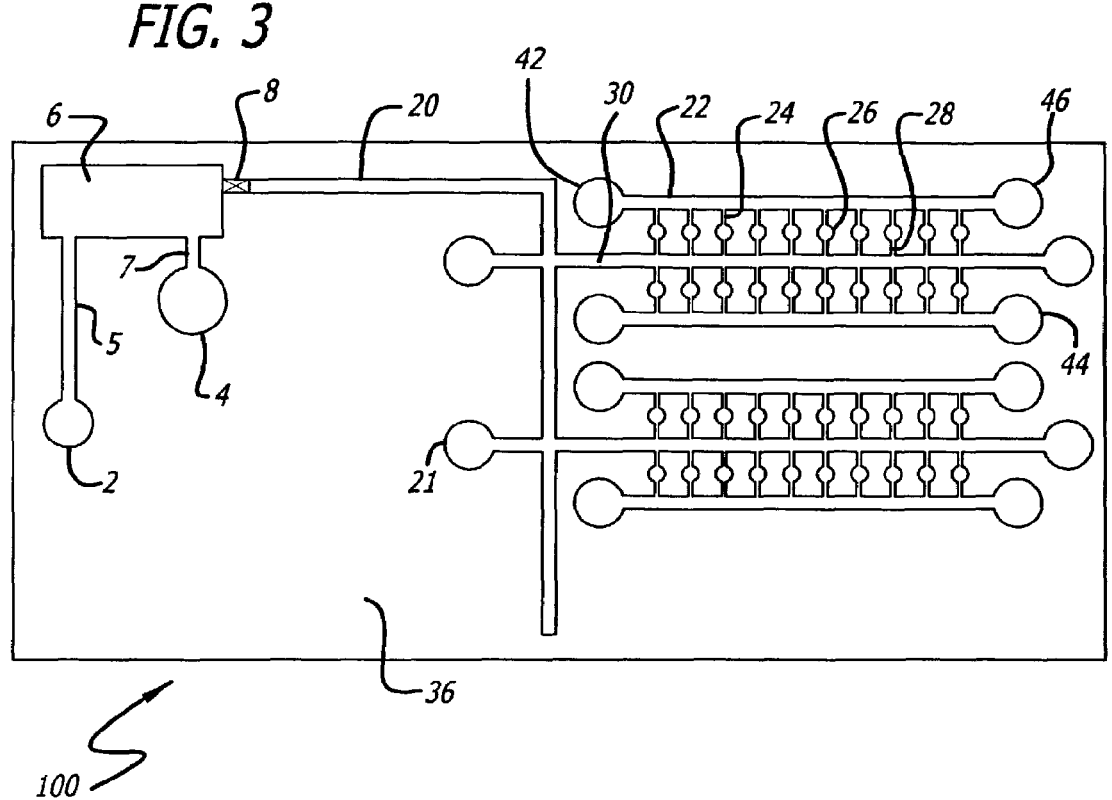
FIG. 3 is a plan view of the upper surface of another sample preparation integrated (SPI) chip in accordance with an alternate embodiment of the present invention.
Figure 4:
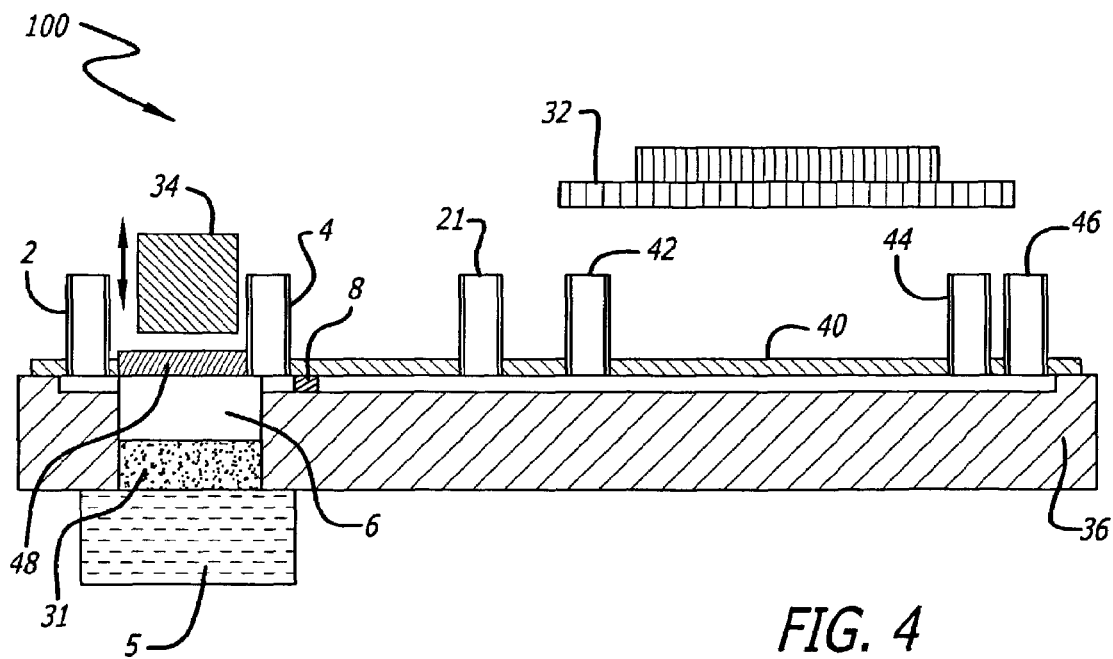
FIG. 4 is a side view of the exemplary chip of FIG. 3.

While FIGS. 7A1-7C-4 depict an exemplary sequence wherein a plurality of assay stations and assay station channels are first filled with sample fluid 56 and subsequently sealed with isolation medium, this is not the only sequence by which the at least one assay station 26 may be filled. In FIG. 7D1-2, the filling of a plurality of assay stations may be accomplished wherein particular assay stations (and assay channels) are sealed while still other assay stations (and assay channels) are at various stages of filling and sealing. For example, in FIG. 7D2, the left-most assay station 26 and assay channels are already filled with sample solution 56 and sealed, while the adjacent assay station and assay channels are filled but only partially sealed by isolation medium 54. These various exemplary sequences are typically achieved by the timing of the introduction of isolation medium 54 into the first and second multipurpose channels. Additionally, differential application of differing types of isolation medium 54, having different flow characteristics, into the first and second multipurpose channels 22 and 30, respectively, may also be utilized to control flow rates through multipurpose channels. Furthermore, differential surface treatments that alter surface energies and interactions with the isolation medium 54 may be utilized to control flow speed, for example.

In addition to the filling and sealing sequences described above, reversed filling of the isolation medium 54 into the multipurpose channels may also be utilized. In this example, sample fluid 56 is introduced, as above, and fills assay station 26, or a plurality thereof. Subsequently, isolation medium 54 is introduced into one of the multipurpose channels and is subsequently cured and/or polymerized and/or solidified, thus providing assay stations having one of their sides sealed by a solidified isolation medium, for example. Subsequently, isolation medium 54 (having the same or different composition than the first introduced isolation medium 54) is then conducted into the opposing multipurpose channel and may be subsequently cured and/or polymerized/solidified. This sequence of sample fluid 56 and isolation medium 54 filling provides for the use of very viscous isolation mediums. Since assay stations and channels are already filled with sample fluid 54 and bounded on one side with a substantially sealed and solid multipurpose channel, the introduction of the second isolation medium 54 into the second multipurpose channel may be accomplished utilizing greater force or pressure upon isolation medium 54 applied secondarily, as the sample fluid will remain in assay station 26 and assay channels 24, 28 and thus not subject to displacement. This provides for the use of very viscous isolation mediums that may require pressurization to be applied in order for them to flow.

Figure 8:
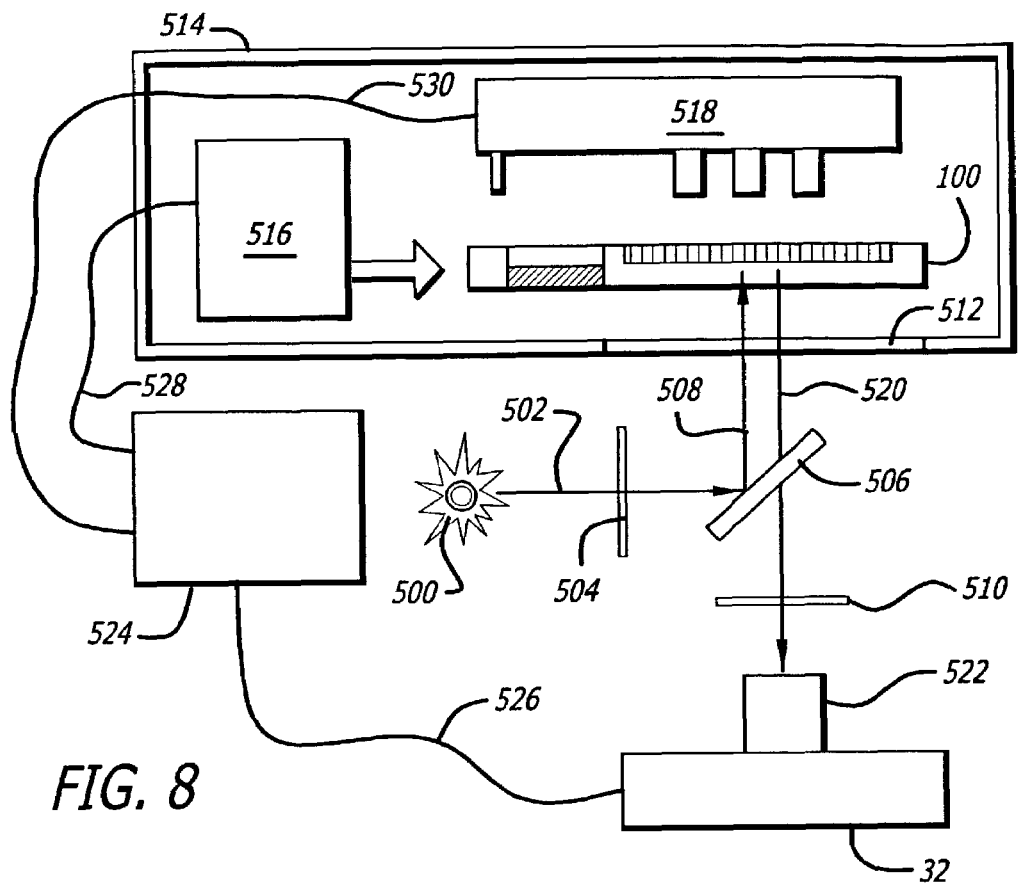
FIG. 8 shows an exemplary analyzer system according to the teachings of the instant invention.

Now turning to FIG. 8, an exemplary analyzer system is shown. This example is particularly use fully when utilizing a fluorescence-based assay, such as PCR, for example. During or at the end of the amplifying of the targeted DNA, some or all of the chip 100 is illuminated by an excitation light source 500 having a wavelength spectrum required to excite the fluorescent dye contained in each assay station 26. The excitation light 502 passes through light filter 504 where it is reflected by optical half-mirror 506. The reflected light 508 passes through transparent window 512 and on to the assay stations. The entire chip 100 is enclosed in an enclosure 514 for thermal control. Thermal control is achieved by temperature control system 516 in conjunction with fluidic handling system 518 which interfaces with the chip 100. The enclosure 514 also includes the temperature control system 516 and the fluidic handling system 518.

When the chip 100 is illuminated by the light source 500, camera 32 detects the fluorescent emission images 520 from all or a subset of the assay stations 26 at camera lens 522. Before the image light 520 reaches the camera lens 522, it passes through filter 510 that filters out all other light and only allows a narrow spectrum of light emitted from the fluorescent dye to pass through and reach the camera lens 522. Camera 32 can be located either above or below the chip 100, although the camera 32 is shown in FIG. 2 and FIG. 4 above the chip 100. As shown in FIG. 8, for PCR amplification of DNA, the detection may be performed at the end of each thermal cycle or after the amplifying process has been entirely completed. The images are analyzed for the fluorescent emission intensity at the location of each assay station, the shape and location of the emission image and the emission intensity. The entire imaging, data acquisition and data processing are controlled by a hardware control computer 524 which is connected to camera 32 by connector 526 and to the temperature control system 516 by connector 528 and to the fluidic handling system 518 by connector 530.

Figure 9:
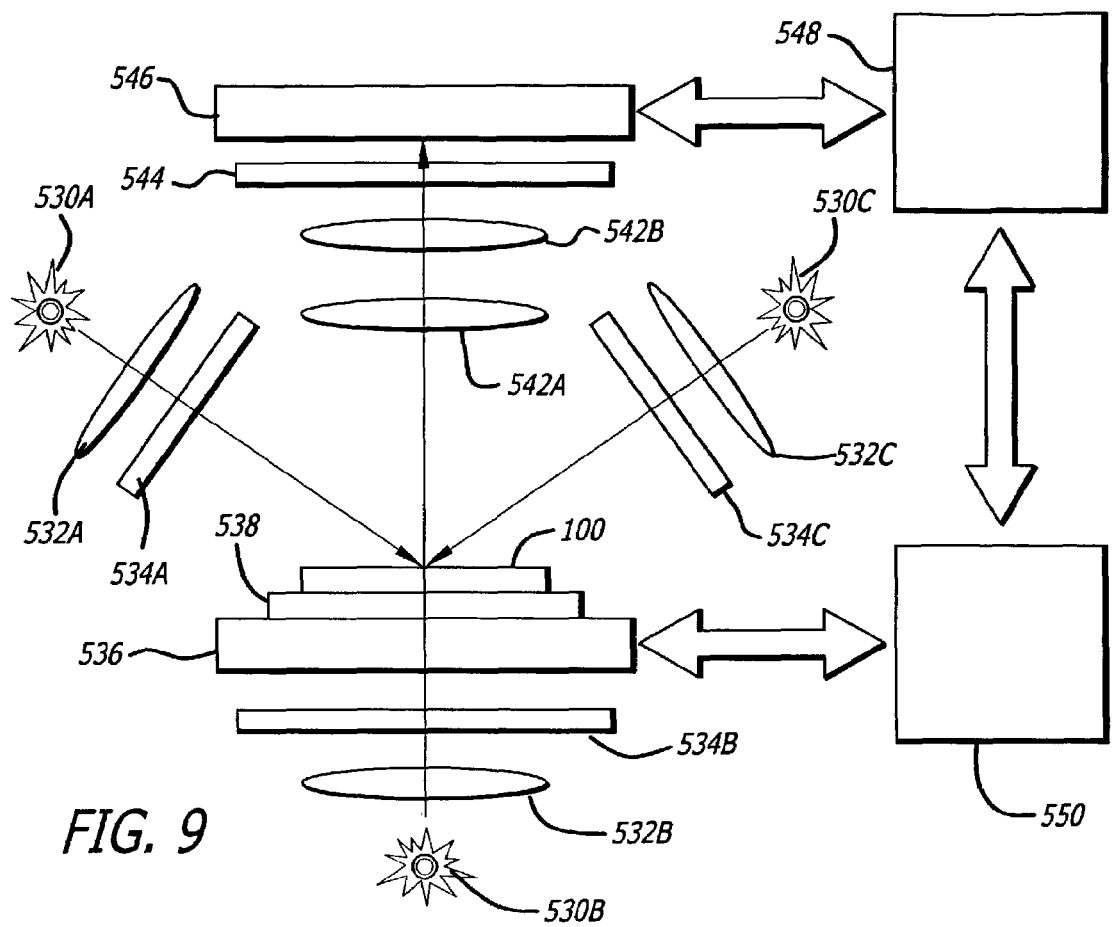
FIG. 9 shows an alternative analyzer system that maybe utilized in accordance with the instant invention.
Figure 10:
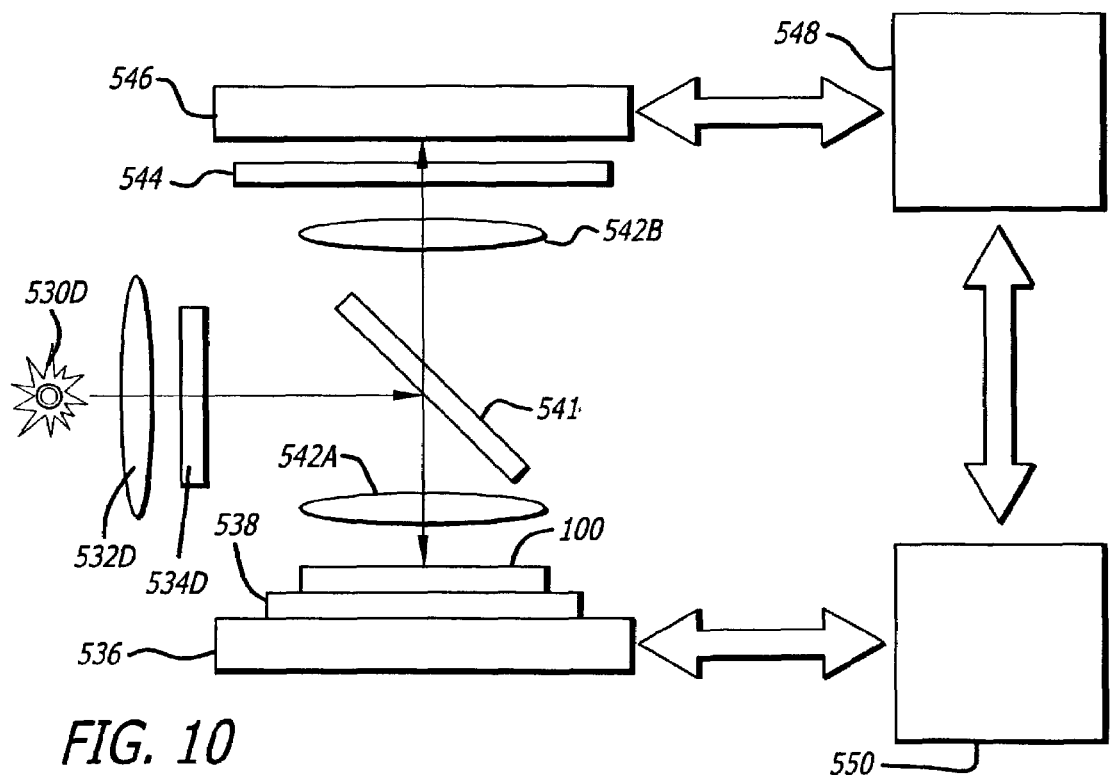
FIG. 10 depicts another exemplary arrangement that may be utilized in accordance with the present invention.

FIGS. 9 and 10 illustrate exemplary arrangement of various components of an analyzer system. FIG. 9 shows a schematic block diagram of a system in which a light beam, which may have comprise an excitation frequency within the excitation spectrum of a fluorophore, illuminates at least one assay station from sides or from the bottom (A, B and C designations of components). Light emitted from source 530A as an excitation beam passes through a beam collimator 532A and a filter 534A, and then strikes onto chip 100 having at least one assay station. Florescent emission from the at least one assay station are imaged to optical sensor 546 by optical capturing assembly 542A and 542B and filter 544. A proportional integral and differential (PID) controlled thermal cycling assembly 538 and a two-dimensional translation stage 536 is connected to microcontroller subsystem 550 then to main computer 548.

FIG. 10 shows a schematic block diagram of a system in which a light beam illuminates at least one assay station from the top. Light emitted from source 530D as an excitation beam passes through a beam collimator 532D and a filter 534D is diverted by dichroic mirror 541 and then strikes on chip 100. Fluorescent emission from at least one assay station is imaged to optical sensor 546 by optical capturing assembly 542B and filter 544. A PID-controlled thermal cycling assembly 538 and a two-dimensional translation stage 536 is connected to microcontroller subsystem 550 then to main computer 548.

In FIGS. 8-10, 500 and 530 light source can be lasers, LEDs (LED Array) or Lamps (CW or pulsed). Beam collimator 532 is preferred to collimate the output light from light source 530. The beam collimator 532 can be a planoconvex lens, for an instance, or it can also be a combination of several optical components such as lenses or lenses in conjunction with optical fiber. After light passes through beam collimator 532, it is filtered by filter 534 which provides excitation wavelength selection together with filter 544 comprise a pair of excitation and emission wavelength band selectors for certain dye, for example, fluorescent-labels. The filter 534 can be a single short pass filter having a cutoff wavelength equal to peak excitation wavelength of the dye. Preferably, a pair of short pass filters of the combination of short pass filter and interference filter are be applied. The filter 544 can be a single long pass filter with cutoff wavelength equal to peak emission wavelength of the dye, or an interference filter with central wavelength equal to peak emission wavelength of the dye.

Figure 11A:
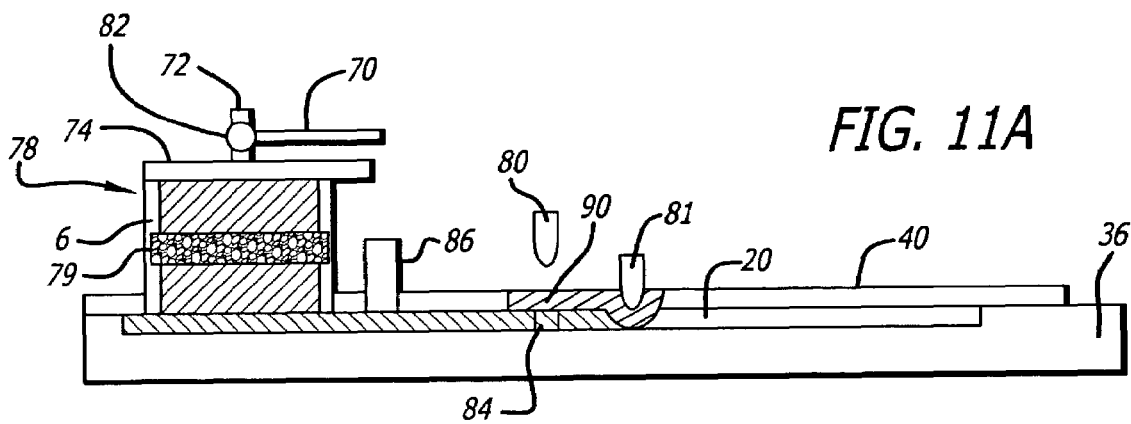
FIG. 11A depicts an exemplary sample fluid preparatory area.
Figure 11B:
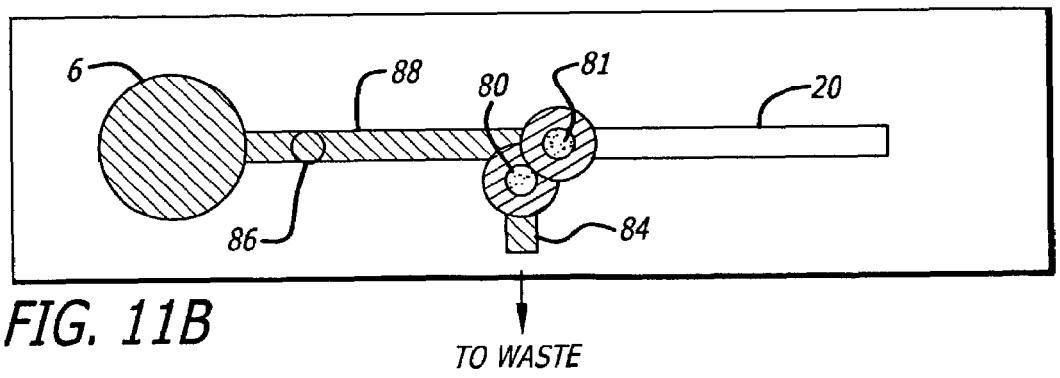

Turning to FIGS. 11A and B depicting particular embodiments, a sample preparation area 78 may be provided upon substrate 36, in fluid connection with sample fluid channel 20. The sample preparation area 78 may be comprised of particular components depending upon the particular type of assay to be run. Accordingly, one embodiment may comprise a sample preparation chamber 6 having a nucleic acid isolation component 79 and a lid 74. Lid 74 may have a flow controlling element 82 in communication with inlets 72 and 70. Either of inlets 72 and 70 may be configured to receive various solutions such as, lysing solutions, buffer solutions and elution buffers, respectively, or one inlet may be provided through which various fluids, including buffers, may be introduced into the sample preparation chamber 6. Nucleic acid isolation component 79 may be comprised of a nucleic acid binding membrane, glass block, magnetic particles or silica beads, for example, as known in the art. Sealing layer 40 may be provided with flexible portions 90 that may be deformed, for example, by a plunger or any machine part that operates with a thrusting or plunging movement, as exemplified by 80 and 81. When depressed into flexible portions 90 of sealing layer, flow to channel 20 or waste channel 84, may be stopped/impeded or allowed to so as to direct fluid flow to one channel or the other.

In the embodiments of FIGS. 11A and B, an air pump for air purging of washing buffer left in chip may be utilized and injected by a "fish pump" controlled by valves.

Furthermore, air pumping of washing buffer and elution buffer may be injected by "fish pump" controlled by valves also.

Typically, sample preparation may be comprised of the following exemplary steps for the embodiment shown in FIGS. 11A and B. For example, if PCR experiments/assays are to be run upon the chip, a solution having nucleic acids therein may be provided into sample preparation chamber 6 having lid 74 removed. Subsequently, lid 74 is replaced upon sample preparation chamber 6 and washing buffer is introduced into sample preparation chamber 6 with plunger valve 81 closed and plunger valve 80 open to guide the washing buffer to waste reservoir by positive pressure or by vacuum, for example. Secondly, one may pump in air from chip inlet 86 to purge remaining washing buffer inside the sample preparation chamber 6 and channel 88 into waste reservoir (not shown) via waste channel 84 (or vacuum the remaining buffer into waste). This results in the nucleic acids binding to nucleic acid isolation component 79.

In order to elute nucleic acids from nucleic acid isolation component 79, a prescribed amount of elution buffer is introduced into sample preparation chamber 6 with plunger valve 80 and 81 closed and chip inlet 86 open to vent air. Air may be pumped into sample preparation chamber 6 to push all the eluent through nucleic acid isolation component 79 and into channel 88. A PCR reaction mixture (comprising for example, dNTPs, buffer and polymerase) may then be added to elution solution via chip inlet 86 and allowed to mix with the elution solution, now containing nucleic acids, thus providing a sample fluid. In a final step, oil may be added into sample preparation chamber 6 and/or inlet 86 and plunger valve 80 closed and plunger valve 81 open to conduct sample fluid having nucleic acid eluted and PCR mix to assay stations via sample fluid channel 20. The sample fluid may also flow to at least one assay station via capillary force, for example and not require the addition of air or liquid pressure.

Figure 12:
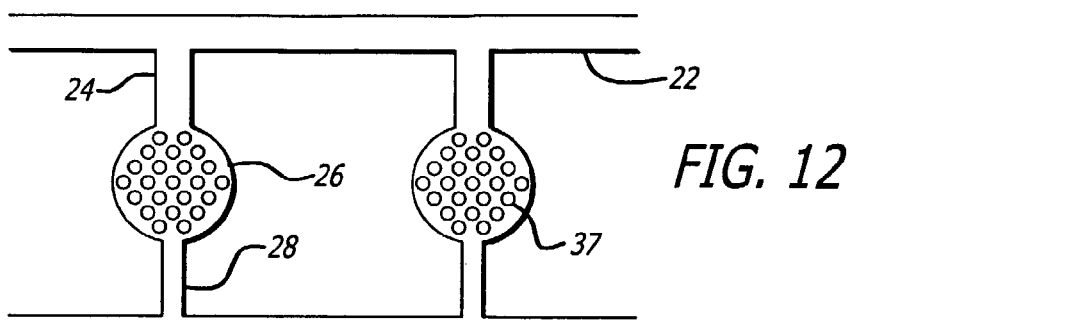
FIG. 12 depicts a top view of assay stations having exemplary flow promoting structures.
Figure 13:
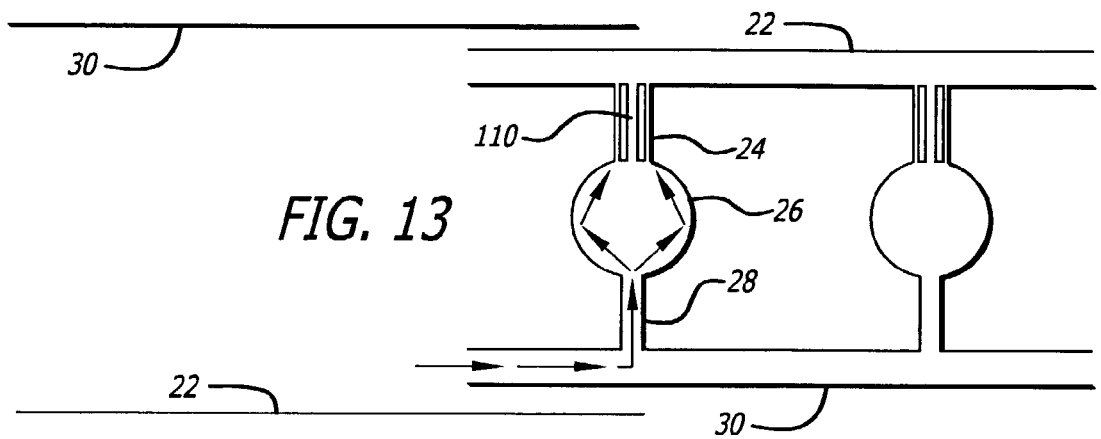
FIG. 13 shows exemplary fluid vent channels of an exemplary assay station configuration.

The assay stations that may be utilized with the instant invention may have a variety of configurations. In FIG. 12, the assay station's central portion is provided with flow promoting structures. These may be comprised of a plurality of nodes 37. These exemplary structures promote even flow of sample fluid 56 into the assay chamber in order to prevent the formation of bubbles within the assay chambers. Flow promoting structures may also be comprised of columns and/or raised protuberances that may be formed upon substrate 36 or sealing layer 40 or both. FIG. 13 depicts fluid vent channels 110 that may be formed within second assay channel conduit. These channels help to divert sample fluid 56 that may enter the assay station too quickly and run along sides assay station 26, as depicted by arrows. In order to prevent the sample fluid 56, which may run along the sides of assay station 26, from meeting at the entrance to second assay channel 24 and forming a bubble, sample fluid would instead flow into second assay channel 24 while a lagging sample fluid front, so to speak, would fill in assay station 26 without bubble formation.

Figure 14:
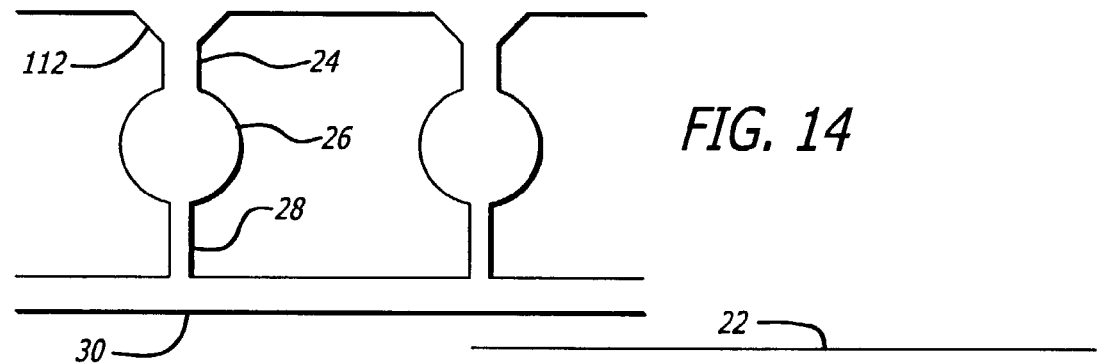
FIG. 14 shows an exemplary bevel that may be provided according to an embodiment.

FIG. 14 depicts another embodiment of assay station 26. Here, second assay channel 24 has adjacent to it a beveled portion 112. Beveled portion 112 provides for complete isolation-medium 54 filling of second multipurpose channel 22, thereby reducing bubble formation that may form as fluid flows past sharp 90° corners and ease of manufacturing. First, if second multipurpose channel 22 has its surface treated in order to impart desired characteristics, such as hydrophobicity, for example, a mask is typically laid over substrate 36 in a manner such that second multipurpose channel 22 is exposed to the applied treatment, such as the application of a coating. However, application of the mask may not be exactly laid out to cover over second assay channel 24 in order for the applied treatment to be restricted to being applied only to second multipurpose channel 22. Having bevel 112 provides for an increased tolerance for the application of the surface treatment, for example, such that if the laying of the mask is not exact, some of the coating may be applied onto the area adjacent the second assay channel 24 and not adversely affect the flow, filling and eventual stoppage of sample fluid 56 into second assay channel 24. Additionally, having such a beveled portion allows for improved flow of isolation-medium 54 through second multipurpose channel 22, allowing for controlled and smooth displacement of air in second multipurpose channel 22 and reduces the likelihood of bubble formation that may occur as a result when second assay channel 24 and second multipurpose channel 22 meet at a sharp corner, such as depicted in FIG. 12 for example.

Figure 15:
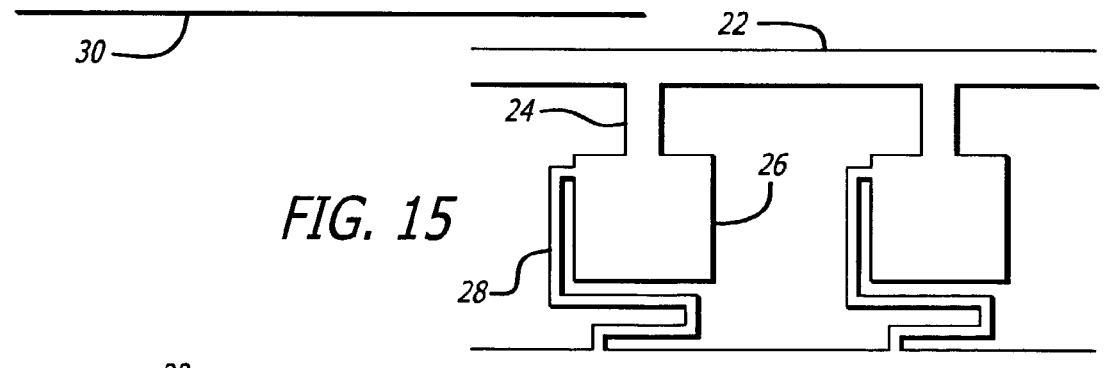
FIG. 15 shows another exemplary embodiment of assay station.

FIG. 15 depicts yet another assay station 26 having an extended first assay channel 28. In this configuration, sample fluid 56 that flows into and fills such assay stations is not subjected to the convective flow that may result in the flow of sample fluid from one assay station to another as a result of heating said sample fluid within assay stations. This is due to the long circuitous path provided by first assay channel 28, which results in the slowing of the flow of sample fluid 56 out of said assay station and into the first multipurpose channel 30, for example. Under particular reaction conditions, isolation fluid may not even be needed to seal assay station and channels from the multipurpose channels.

Figure 16:
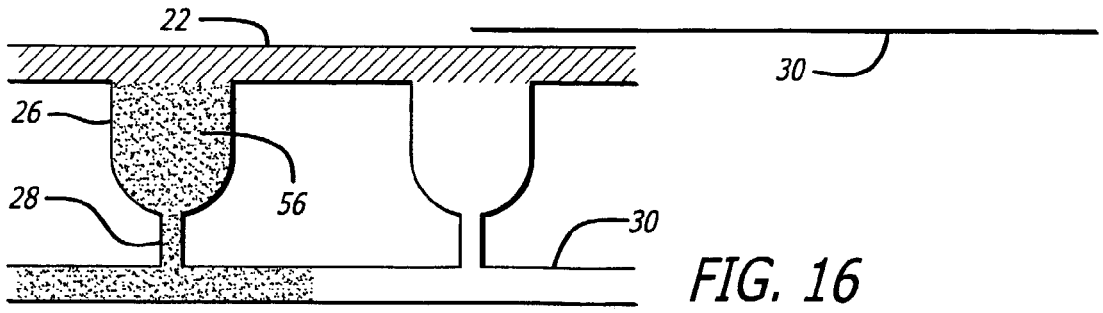
FIG. 16 depicts still another exemplary embodiment of assay stations in accordance with the teachings of the invention.

FIG. 16 depicts another exemplary configuration of an assay station 26, wherein an arrangement of at least first and second multi-purpose channels is provided. At least one assay station 26 is situated in a position intermediate between a first and second multipurpose channels and is in fluid communication therewith. Here, first multi-purpose channel 30 has internal surface characteristics conducive to conduction of a sample fluid therethrough while second multipurpose channel 22 may have a hydrophobic surface characteristic that is not conducive to conduction of sample fluid therethrough. The forces/surface characteristics are strong enough to repel sample fluid 56 and retain it in the assay station 26. Assay station channels 24 and 28, as well as the other channels, may have other exemplary configurations such as triangular, ellipse and lozenge-type cross-sectional configurations in addition to circular, semicircular or other cross-sectional shape.

The method of detecting disease or assessing the risk of disease of the present invention comprises the following exemplary steps. A test sample of whole blood, for example, from an animal is obtained from a subject. Before the analysis, each assay station on the chip device 100 may have deposited at least one of a specific probe and primer(s), and each assay station is dried. So there is at least one DNA probe and/or primer in all of the assay stations 26 on chip 100. Each assay station 26 contains at least one probe or primer (some assays, for example, FRET, requires two primers and 1 or 2 fluorescent dye-labeled probes).

A quantity of the test sample whole blood obtained from the subject is provided onto the device by e.g. injection. The quantity of blood sample applied to the device can be determined by the skilled artisan based on the number of assay stations to be filled. But in general, the amount of blood applied will be sufficient to completely fill the assay stations provided on the chip. Typically, about 0.01 ul to about 10 ml of sample will be sufficient to carry out the methods of the present invention. By "application" or "applied" is meant that the sample is provided to the device by conventional means including injection, electro-osmosis, pressurization, or vacuum means.

A gas and/or fluid is injected into sample preparation chamber 6 via test sample inlet 2 exclusively with buffer inlet 4 closed, or else with buffer inlet 4 initially open until buffer inlet 4 is filled, after which it is closed, to purge the elution buffer containing released DNA molecules and push the buffer into an empty chamber 12 and completely fill chamber 12. Examples of gases and/or fluids suitable for the methods of the present invention include, but are not limited to air, carbon dioxide, nitrogen, argon, or a purging liquid like oil. A flow promoting fluid (FPF) in chamber 16 is then released into chamber 12 through diffusion channels 14.

DNA contained in buffer (now sample fluid) will flow into channel 20 and further flow into first multi-purpose channel 30, first assay station channel 28 and assay station 26.

The digital camera 32 detects the time when all the assay stations 26 are filled by buffer. Isolation medium 54 is injected through at least one of ports 44, 46 into channels 30 and 22 to fully fill the multipurpose channels. Again, the isolation medium 54 typically can be wax, oil, phase-changing plastics, thermally curable polymer liquid, or ultra-violet (UV) curable polymer liquid. The isolation medium remains at an elevated temperature above about 100° C. via preheating and/or the chip 100 is in an environment of an elevated temperature. Typically, when the isolation medium is wax, the wax is pre-heated to a particular temperature, since a medium like wax does not flow in its solid phase. However, other materials like thermal curable and UV curable resin are in liquid state at a room temperature and therefore these materials do not require pre-heating. All assay stations are placed in a thermal cycler and subjected to PCR according to known methods. See e.g. Ausubel et al. *Current Protocols in Molecular Biology*, Greene Publishing Associates and Wiley-Interscience, John Wiley & Sons, New York, 1995, incorporated herein by reference. Following DNA amplification, at least a portion of the device is illuminated by an excitation light source having a wavelength spectrum required to excite the fluorescent dye, e.g. fluorescein, contained in each assay station 26. When the illumination is performed, camera 32 detects the fluorescent emission images from each assay station 26. The fluorescent emission images are analyzed for: fluorescent emission intensity at the location of each assay station 26, shape and location of the fluorescent image and the emission intensity of the image in each assay station.

The main components of the analyzer are the fluorescent emission detection camera and the related optics which are available commercially, for example, from Hamamatsu, 325-6, Sunayama-cho, Hamamatsu City, Shizhoka Pref., 430-8587, Japan. The camera and the optics system are installed in an enclosure together with a liquid handling system for liquid/sample injection. The analyzer also includes a temperature control system to perform thermal cycling required for PCR amplification of DNA molecules.

EXAMPLE

An exemplary method of preparing the sample and extracting DNA from the test sample is illustrated in the following example, exemplarily illustrated in FIGS. 1-4:

Step 1. Injecting the sample:

Sample, for example, a test sample (e.g. whole blood), is injected into sample preparation chamber 6 via test sample inlet 2. The injection in this step can be achieved by means such as pressurization, capillary pumping, or vacuum suction (a vacuum is conventionally generated below glass block 31).

Step 2. Lysing of cells and binding of DNA on porous glass block 31

Cell lysing buffer is injected into sample preparation chamber 6 via inlet 4. Cell lysing buffer lyses both red cells and white cells in sample and DNA molecules are released from the white cells, and become suspended in the lysing buffer contained in sample preparation chamber 6.

One example of the cell lysing buffer contemplated by the present invention is:

(1) For lysing of red blood cells (Buffer A):
  (i) 4.15 g of $NH_4Cl$ dissolved in 500 ml of water and Tris-HCl adjusted to pH 7.2.
  (ii) Make a separate stock by dissolving 2.06 g of Tris base into 100 ml water adjusted to pH 7.2.
  Mix (i) and (ii) in the volumetric ratio of 9:1
(2) For lysing of white blood cells (Buffer B): 6M GuSCN (guadinine isothiocyanate) and 10 mM EDTA The above buffers "A" and "B" can be added together or in sequence "A" before "B" or "B" before "A".

Another lysing buffer contemplated by the present invention is:

1 part of 10% Triton X-100, dilute to 10 parts using 6M GuHCl (guadinine hydrochloride) (in 10 mM TE, pH 6.7).

Sample can also be mixed with lysing buffer before being injected into sample preparation chamber 6. The lysed whole blood sample (together with the lysing buffer) in sample preparation chamber 6 is sucked through the glass block 31 due to the absorption by the absorbent 5 or by vacuum. When the lysed sample passes through the glass block 31, DNA molecules in the lysed sample are bound to the surface of the glass block 31, since the glass block 31 has the ability to attract DNA contained in sample.

In addition to the absorption and the vacuum means described above to pass the lysed sample and lysing buffer through the glass block 31, the following means can also be applied: positive pressurization, such as that generated by a syringe pump, to pump the sample and lysing buffer through the block 31 or electro-osmosis pumping.

The glass block 31 can also be replaced by other filter media including: glass fiber mat or floss, glass powders, non-glass media such as cellulose fiber mat, or magnetic particles with treated surfaces to attract DNA molecules, etc. The glass block 31 can also be made of a combination of filter media. The DNA attraction mechanism on the filter media can be in the form of, for example, electrostatic attraction or attraction of DNA to other molecules pre-immobilized onto the filter media.

Step 3. Washing the chamber 2 and glass block 31

Washing buffer is injected to sample preparation chamber 6 via buffer inlet 4, and washing buffer is pulled through the glass block 31 due to the absorption by the absorbent 5 or by vacuum. Under the flow of the washing buffer, the DNA molecules bound to the glass block 31 still remain, while all other substances including cell debris or proteins in sample preparation chamber 6 and glass block 31 flow through to a waste drain, which can be the absorbent 5 itself, underneath the glass block 31. At the end of this washing step, only isolated DNA molecules are collected for subsequent use.

One example of washing buffer contemplated by the present invention is 200 mM NaCl, 20 mM Tris-HCl, 5 mM EDTA, adjust pH of mixture to 7.5. Dilute mixture with 95% ethanol in the volumetric ratio of 1:1.4 (eg: add 40 ml ethanol to 100 ml buffer). Another washing buffer contemplated by the present invention is 80% isopropanol.

In addition to the absorption and the vacuum means described above to pass the washing buffer through the glass block 31, the following means can also be applied: positive pressurization such as that generated by a syringe pump to pump the washing buffer through the block 31 or electro-osmosis pumping.

Step 4. Eluting DNA from glass block 31

After the glass block 31 is dried, the elution buffer is injected into sample preparation chamber 6 via buffer inlet 4 to fully occupy sample preparation chamber 6. The drying is performed by methods such as natural drying or by elevating the ambient temperature or by hot air blowing. The drying duration typically ranges from a few seconds to a few minutes. Injection of the elution buffer can also be performed by injecting the buffer into the sample preparation chamber 6 through the glass block 31 ("bottom up", i.e., injected in the upward direction through the glass block 31).

The elution buffer is capable of releasing attracted DNA molecules from glass block 31, and the DNA molecules released become suspended in the elution buffer contained in sample preparation chamber 6 above the glass block 31. One example of the elution buffer is autoclaved water. Another example of the elution buffer is 10 mM TE at pH 8.4.

To enhance the elution efficiency, a vibrating actuator 34 presses diaphragm 48 to agitate the elution buffer in the sample preparation chamber 6 and glass block 31 to allow more DNA molecules to leave the glass block 31 and enter the elution buffer.

The present invention also contemplates soaking the glass block 31 in elution buffer for about five minutes.

The elution buffer can contain, or be added with other chemicals for subsequent analysis, (such additional chemicals can be added by premixing such chemicals with the elution buffer, then by adding the mixture to sample preparation chamber 6 subsequently via test sample inlet 2 and/or buffer inlet 4). Additional chemicals contemplated include the enzymes for DNA amplification, fluorescent dye for fluorescent detection of DNA molecules based on principle of fluorescence energy resonance transfer (FRET), TaqMan® (Roche Molecular Systems, Inc., Somerville, N.J.), SYBR Green® (Molecular Probes, Inc., Eugene, Oreg.), and Molecular Beacon, and any other chemicals required to perform DNA amplifications and fluorescent detection. The injection in this step may be achieved through pressurization, capillary pumping, vacuum suction, etc.

The amount of elution buffer should fully occupy the sample preparation chamber 6 so that the elution buffer can reach the inlet of the channel 10, as shown in FIG. 1. Since there exists a valve 8, the elution buffer is confined to sample preparation chamber 6 during this operating step.

All efforts should be made to prevent the elution buffer from moving outside the domain of the chamber 6, since this would cause the loss of DNA molecules for subsequent analysis. (In particular, inadvertent application of the absorbent 5 should be avoided).

To enhance the spread rate of DNA molecules into the entire volume of the elution buffer and to enhance the uniform distribution of the DNA molecules in buffer, the following methods can be used in the alternative: agitating buffer by actuator 34 acting on diaphragm 48, as described above; applying a vibrator to shake the entire substrate 36 (chip) at one or more than one vibration frequencies, especially at a resonant frequency of (1) the entire chip, and (2) the mass of the elution buffer contained in sample preparation chamber 6; heating the buffer contained in sample preparation chamber 6 non-uniformly to generate a thermal-gradient induced flow, or forced convection flow, of the buffer inside sample preparation chamber 6; adding surfactant to the buffer contained in sample preparation chamber 6 to help to release the DNA molecules from the glass block 31; or adding magnetic beads or fibers into buffer and using an electromagnetic actuator to agitate the buffer to help to release the DNA from the glass block 31.

In all of the above steps, test sample inlet 2 and buffer inlet 4 can be used interchangeably, or a single port (i.e. test sample inlet 2 or buffer inlet 4) can be employed to conduct the methods of the present invention.

While the description has been generally directed to PCR and other amplification assays, the invention is by no means so limited. The apparatus and methods of the present invention may also be utilized to conduct a plethora of various assays, including homogeneous assays. Homogeneous assays which may be performed on the chip can be divided into 3 general categories: DNA/RNA/Aptamers (nucleic acid based), Protein/antibody based and cell based assays. Exemplary assays and components are provided below.

In DNA/RNA/Aptamers (nucleic acid based) embodiments, primers and probes in 0.1×TE buffer, for example, were spotted/placed into the assay stations 26 and then lyophilized. Immobilization of at least one reaction component within at least one assay station may also comprise, for example, immobilization onto beads, gels or membranes. Sample fluid preparation releases DNA or RNA into a PCR reaction mixture (minus primers and probes) and the whole mixture flows into the assay stations via first multi purpose channel 30 or channels. Upon rehydration the primers and probes participate in the PCR or if specified, RT-PCR reaction. Detection of products may be conducted by, and not limited to, utilizing fluorescence resonance energy transfer (FRET), molecular beacon detection, or normal non-FRET SybrGreen, EtBr detection or other intercalators (PicoGreen, the TOTO dye family e.g. Toto-1, POPO-1, BOBO-1) for example. Real-time data of DNA or RNA amplification is collected during each cycle and then subtracted from a baseline.

In exemplary DNA based assays, amplification and detection methodologies may comprise PCR, isothermal amplification methods e.g. nucleic acid strand-based amplification (NASBA), strand displacement amplification (SDA), etc, as well as ligase chain reaction (LCR), rolling circle amplification and ligation, etc., using FRET, molecular beacon, etc. as described above.

All of the following assays that may be conducted in accordance with the teachings of the present invention are meant to be exemplary and non-limiting.

DNA Based Assays

Example 1

PCR Assay with Sybrgreen in Assay Stations (Diameter ~0.5-1 mm), chip thickness ~2 mm:

PCR mix: 1 ul of 10×Pt Taq polymerae buffer, 0.8 ul of 25 mM $MgCl_2$, 1 ul each of 10 uM stock Trytophan hydroxylase, Forward primer (5'-TGT GTT AGC CAT TAT GAT TA 3') and reverse primer (5'-CTG GAA TAC AAG CTT TAT GCA G-3'), 1 ul of 2 mM dNTPs, 1 ul of long/ul human genomic DNA, 0.5 ul of 10%BSA, 0.5 ul of 60×SybrGreen, 1 ul of 5u/ul Platinum Taq Polymerase and 2.2 ul water. In the control, the above components are the same except there is no Taq polymerase.

PCR conditions: hot start 96° C.—1 min, 30 cycles of 95° C.—30 sec, 55° C.—30 sec. and 72° C.—30 sec, 72° C.—5 min, 12° C.—forever. PCR was done in a MJ PCR thermocycler (PTC-200) with an in-situ PCR alpha module. After PCR, the chip 100 was observed under a Leica fluorescent microscope using the same exposure time for each image, hooked up to a computer for digital image capture. The results showed positive amplification of human Tryptophan hydroxylase gene fragment as compared to control reactions.

Example 2

PCR-FRET detection of the 23S RNA gene from *Plesiomonas shigelloides*, a Gram-negative bacteria that causes human gastroenteritis. Reference: J. P. Loh and Eric P. H.

Yap, Rapid cycle Real-Time PCR, Methods and Applications, Microbiology and Food analysis, U. Reischl et. al. (Eds.), Springer, pp 161-171.

PCR mix: 1 ul of 10×Platinum Taq buffer, 1 ul of 2 mM dNTPs, 0.3 ul each of 10 uM stock forward primer (5'-AGC GCC TCG GAC GAA CAC CTA-3') and reverse primer (5'-GTG TCT CCC GGA TAG CAC-3'), 1 ul of a 20 uM stock fluorescent probe (5'-LCRed640-GGT AGA GCA CTG TTA AGG CTA GGG GGT CAT C-3'-Phosphate), 1 ul of 5 ug/ul BSA, 1.6 ul of 25 mM Mgcl2, 1 ul of 10×Sybrgreen, 0.1 ul of 5u/ul Platinum taq, 1.2 ul of water and 1,5 ul of sample containing P. shigelloides DNA.

PCR conditions Hot start: 95° C.—1 min, 70 cycles of 90° C.—0 sec, 70° C.—4 sec , 72° C.—5 sec.

Single Nucleotide Polymorphism (SNP) detection: Allele-specific PCR, dye-labeled oligonucleotide ligation (DOL), PCR-OLA-FRET (oligonucleotide ligation assay), LCR-OLAFRET, allele specific Taqman assay, etc.

Example 3

Dye-labeled oligonucleotide ligation (DOL) assay is an assay that uses PCR to amplify the DNA sequence and then post-PCR SNP detection using OLA or oligonucleotide ligation assay with FRET (PCR-OLA-FRET). The OLA assay uses 3 probes to detect a SNP, one common donor probe is labeled with FAM (5-carboxy-fluorescein), and the other allele-specific acceptor probe labeled with either ROX (6-carboxy-X-rhodamine) or TAMRA (NNN8,N8-tetramethyl-6-carboxyrhodamine). Thermostable ligase was used to discriminate between a match or mismatch nucleotide at the 5'-of the acceptor probe. Reference: X. Chen, et.al., Genome Res. May 1998;8(5):549-56.

DOL assay for detecting codon 39 C/T mutation in the beta-globin gene responsible for beta-o-thalassemia. The primers and probes were lyophilized in the assay stations and the DNA from sample prep portion was infused into the assay stations via the various channels described above.

PCR-ligation mix: 2 ul of 100 mM Tris Ph 8.0, 2 ul of 65 mM MgCl2, 2 ul of 0.5M KCl, 2 ul of 10 mM NAD, 2 ul of 2.5 mM dNTPS, 1 ul of each 50 uM stock PCR forward primer (5'-CAT GTG GAG ACA GAG AAG ACT CTT GGG-3') and reverse primer (5'-GCA GCT CAC TCA GTG TGG CAA AGG-3'), 1 ul of 4 uM FAM-labeled donor probe (5'-FAM-TCT ACC CTT GGA CC-3'), 1 ul of 4 uM Rox-labeled acceptor probe (5'-phosphate-CAG AGG TTC TTT GAG T-3'-ROX), 1 ul of 5 uM TAMRA-labeled acceptor probe (5'-phosphate-TAG AGG TTC TTT GAG TC-3'-TAMRA), 30 ng of human genomic DNA, 0.5 unit of AmpliTaq-FS polymerase, 1.5 unit of Ampligase DNA ligase and water to 20 ul.

PCR-ligation conditions: Denaturation 95° C.—2 min, 10 cycles of 95° C.—15 sec, ramping slowly to 65° C. over 1.5 min, 65° C.—30 sec, followed by 30 cycles of 95° C.—15 sec, 65° C.—30 sec, and ligation using 25 cycles at 95° C.—15 sec, 45° C.—1.5 min.

RNA Based Assays

Example 1

Amplification and detection: RT-PCR-FRET detection of Dengue virus type II. Reference: B. H. Tan, E. See, Elizabeth Lim and Eric P. H. Yap, Rapid cycle Real-Time PCR, Methods and Applications, Microbiology and Food analysis, U. Reischl et. al. (Eds.), Springer, pp 241-251.

RT-PCR mix: 2 ul of 5×RT-PCR buffer, 1 ul of 3 mM dNTPs, 1 ul of 5 ug/ul BSA, 1 ul of 25 mM MnOAc, 0.5 ul each of 9 uM stock forward primer (5'-CCT AGA CAT AAT CGG G-3') and reverse primer (5'-GTG GTC TTG GTC ATA G-3') and 0.5 ul of 4 uM stock probe (5'-LCRed640-AGA AAA AAT AAA ACA AGA GC-3'-Phosphate), 0.5 ul of 20× SybrGreen, 0.5 ul of 5 ul/ul Tth polymerase, 1.5 ul water and viral RNA added to 10 ul final volume.

RT-PCR conditions: RT—15 min at 50° C., denaturation 95° C.—5 min, 8 cycles of 95° C.—0 sec and 55° C.—7 sec, 50 cycles of 87° C.—0 sec, 55° C.—7 sec.

Aptamer Based Assays:

Aptamers are synthetic DNA, RNA or peptide sequences which may be normal and modified (e.g. peptide nucleic acid (PNA), thiophophorylated DNA, etc) that interact with a target protein, ligand (lipid, carbohydrate, metabolite, etc). Aptamers labeled with a dye, e.g. TAMRA for example, may be synthesized and spotted into assay chamber 26 or chambers and lyophilized. A target protein/antigen may then be introduced into the assay stations utilizing methods as described above. Fluorescent polarization may then be utilized to screen for aptamer/protein binding if one of the binding pair is labeled with the fluorescent dye.

Protein/Antibody Based Assay

Protein/Antibody assays, such as ELISA (enzyme-linked immunosorbent assay) may be utilized according to the teachings of the present invention to detect pathogens (e.g., open sandwich ELISA), protein-rich interactions and drug screenings.

In these exemplary embodiments, the antibodies or proteins can be labeled with pairs of FRET dyes, bioluminescence resonance energy transfer (BRET) protein, fluorescent dye-quencher dye combinations, beta gal complementation assays protein fragments, and dissolved in 1×PBS, spotted and lyophilized in the assay stations. Sample fluid preparation releases proteins or other antigens into PBS or TBS buffer with or without detergent (e.g. Tw-20 or Triton-X 100) of various concentration (e.g. 0.05% Tw-20 and 1%Triton-X-100), and these flow into the assay stations via channels as described above. Upon re-hydration the antibodies or protein pairs may participate in FRET, BRET, fluorescence quenching or beta-gal complementation to generate fluorescence, colorimetric or enhanced chemiluminescence (ECL) signals.

Example 1

Antibody-antigen fluorescence quenching assay: An antibody was labeled with OG-514 (Oregon green 514 carboxylic acid, succinimidyl esters) and the antigen (peptide, protein, whole cells, carbohydrate, aptamers, etc.) was labeled with QSY-7 (QSY-7 carboxylic acid, succinimidyl esters). Fluorescence quenching prevented or suppressed the detection of OG-514 fluorescence. The labeled antibody-antigen complex was lyophilized in the assay stations. Sample fluid preparation releases proteins or other antigens into PBS or TBS buffer with or without detergent (e.g. Tw-20 or Triton-X 100) of various concentration (e.g. 0.05% Tw-20 and 1%Triton-X-100), and flow into the assay station(s) via channels. Upon re-hydration in the assay station, the labeled antibody-antigen complex participates in competitive reaction with the unlabeled antigen. Competition with unlabeled antigen releases the OG-514 labeled antibody whose fluorescence is detected at about 528-530 nm.

Example 2

Double Sandwich Antibody FRET

Two monoclonal antibodies directed against 2 non-competitive epitopes of the CD8-alpha chain were utilized. One of the monoclonals was labeled with the dye phycoerythrin (PE) and the other allophycocyanin (APC).

FRET was observed when excitation light was directed to PE but the efficiency was only 10%. Reference: Batard P., et.al., Cytometry Jun. 1, 2002;48(2):97-105. The efficiency of FRET may be improved by using near Infra-red FRET dye pairs such as the squaraine dyes (Sq635 and Sq660). Reference: Oswald B. et. al., Analytical Biochemistry 280, 272-277 (2000).

Example 3

Re-association of recombinant antibody light and heavy chain directed by a bridging antigen (open sandwich assay).

Recombinant antibody anti-HEL (Hen egg lysozyme) fragment heavy chain (VH) and light chain (VL) were labeled with succinimide esters of fluorescein and rhodamine-X, respectively. The weak affinity of VH and VL towards each other prevent association and FRET, but at low temperature e.g. about 4C and in the presence of antigen, the VH and VL interactions stabilized and hence FRET occurred. When excited at 490 nm, significant decrease in the fluorescence at 520 nm and its increase at 605 nm were observed when an increasing amount of HEL (antigen) was added to the mixture in the concentration range of 1-100 micrograms/ml. Reference: Ueda H et. al., Biotechniques Oct. 1999;27(4):738-42.

A modification of the above method may be utilized as follows. Instead of labeling with fluorescent dyes such as fluorescein and rhodamine, chimeric protein of VH—Rluc (Renilla luciferase) and VL-EYFP (Enhance Yellow fluorescence Protein) is constructed. In the presence of Rluc's substrate coelenterazine, chemilumiscence with emission of light (475 nm) is observed, but no BRET (Bioluminescence fluorescent energy transfer) is observed. However, at low temperature e.g. about 4° C. and in the presence of antigen (HEL), the VH and VL interactions was stabilized, hence BRET occurred and fluorescence of EYFP is detected at 525 nm. Reference: Arai R, et. al., Anal Biochem. Feb. 1, 2001;289(1):77-81.

Yet another modification of the first method is as follows. Instead of labeling with fluorescent dyes such as fluorescein and rhodamine, thioredoxin (Trx) fusion protein protein, Trx-VH-EBFP (enhance blue fluorescent protein) and Trx-VL-EGFP (enhance green fluorescence protein) is constructed. Trx increased the solubility of the expressed proteins. FRET occurred in the presence of the antigen HEL. Reference: Arai R., et. al., Protein Eng. May 2000;13(5): 369-76.

The apparatus and methods of the present invention may also be utilized to conduct proteomic studies/assays. Protein-protein interactions are important mechanisms for regulating cellular process, e.g., regulation of transcription by the dimeraztion of basic helix-loop-helix (bHLH) transcription factors, dimerization of Epidermal growth factor (EGF) receptor upon ligand binding to generate cellular signaling, for example.

Utilizing the apparatus, candidate proteins or 'Preys' expressed as fusion proteins with enhanced green fluorescent protein (EGFP), for example, may either be lyophilized in assay staions or embedded into hydrogels in the assay stations. The target or 'bait' expressed as fusion protein with enhanced blue fluorescent protein (EBFP) is introduced into the assay stations through the channels as described above. Protein-protein interaction activates FRET activity, for example or other detection methods, as known in the art.

Cell-Based Assay:

The present invention may also be utilized in drug screening and toxicological assay applications. Numerous methods for drug screening based on FRET, and other detection methods may be utilized as known to those of ordinary skill in the art.

For example, toxological assays may be conducted according to the teachings of the present invention. Synthetic small molecules from combinatorial chemical, or peptide library, aptamer library, etc, are pre-loaded into the assay stations. The assay stations have conducted thereto particular cell type of interest, which may have been recovered from a sample preparation portion of the chip (if so provided), or from tissue culture, growth media. A fluorescent vital dye may also be provided. After a few days observation with microscopy will reveal if cells exposed to the provided pre-loaded components undergo cell death remain alive or are otherwise affected by the pre-loaded assay components that had been provided in the assay stations.

For drug screening, cells can be engineered to express the drug target to be tested e.g. multi-subunit receptor, heterodimerizing or homodimerizing protein partner, fused with different fluorescent protein (e.g. EGFP, EYFP). Association or cross linking of receptors or proteins with themselves or to their subunits triggered by synthetic ligand binding, small molecule or antibody, brings the fluorescent protein pair together such that FRET can take place or beta-gal complementation could occur, for example. Conversely, disruption of homodimerized or heterodimerized or multi-subunit protein complex by synthetic ligands, small molecule, aptamer, etc., could trigger a decrease in FRET signal.

The small molecules may diffuse into cells depending on the chemical structure. Hence, target protein does not need to be a surface proteins, but can be an intracellular protein or receptor, such as glucocorticoid receptor, that homodimerize in the presence of glucocorticoid, for example.

The small molecules, ligand, aptamer, etc. may be derived from a combi-chem library, peptide synthesizer, phage library, etc. and are first spotted into the assay station and then lyophilized. Cells engineered with a drug target protein fused to green fluorescent protein (GFP) pairs are then introduced into the assay station(s) 26 via channels, as described above, in cell culture media. Incubation of the cells with the potential drug at about 37C, for example, may trigger protein-protein interaction resulting in FRET, or disruption of protein interaction would decrease FRET.

Drug screening applications according to the invention may utilize cell based and/or protein assays. Such screening applications may utilize the introduction of at least one of a population of wild-type cells and a population of cells expressing a recombinant molecule, for example, into said at least one assay station, in accordance with the teachings of the present invention.

Besides FRET assays which utilized two fluorescent probes for PCR, PCR-Taqman assays make use of fluorescent quenching whereby a probe is labeled with both quencher and donor. The probe, when hybridized to amplified DNA fragments, is digested by the 5' to 3' exonuclease activity of Taq polymerase extending downstream from the primer. Upon digestion of the probe, separation of donor from quencher leads to a detectable increase in fluorescence signal from the donor dye. Colorimetric detection can potentially be used in conjunction with beta-gal complementation assays in isothermal amplification assays. Another exemplary assay methodology that may be utilized includes fluorescence polarization, wherein small fluorescent dNTPs are incorporated into PCR product, for example, and as a result tumble less and decrease their effect on the depolarization of light applied to the assay station 26 having the PCR mixture and potential product therein and subsequently detected.

The invention has now been explained with reference to specific embodiments. Other embodiments will be apparent to those of ordinary skill in the art in view of the foregoing description. It is not intended that this invention be limited except as indicated by the appended claims and their full scope equivalents.

We claim:

1. An apparatus comprising:
   a substrate having a least one assay station;
   an arrangement of at least one first multipurpose channel and at least one second multipurpose channel wherein said at least one assay station being situated in a position intermediate between said first and second multipurpose channels and in fluid communication therewith, wherein said first multipurpose channel has at least one surface characteristic conducive to conduction of a sample fluid therethrough and into said at least one assay station;
   at least one sample fluid inlet in communication with said at least first multipurpose channel;
   at least one isolation-medium inlet in communication with said at least first and second multipurpose channels to enable isolation medium to flow along said at least first and second multipurpose channels to isolate said at least one assay station after conduction of the sample fluid into said at least one assay station, said at least one second multipurpose channel having at least one surface characteristic non-conducive to conduction of said sample fluid; and
   at least one isolation medium outlet in communication with each of said first and second multipurpose channels, thereby allowing the isolation medium to flow in to said first and second multipurpose channels by purging the sample fluid in said first multipurpose channel and air in said second multipurpose channel through respective said outlets.

2. The apparatus of claim 1 wherein said fluid communication is via at least first and second assay station channels in communication with said first and second multipurpose channels.

3. The apparatus according to claim 2 wherein said internal surface of said second multipurpose channel and a surface of said second assay station channel immediately adjacent to the intersection of the second assay station channel and said second multipurpose channel are non-conducive to conduction of said sample fluid.

4. The apparatus of claim 3 wherein said first and second multipurpose channels provide a path by which said plurality of assay stations are sealed via the flow through of an isolation medium.

5. The apparatus according to claim 2 wherein said at least first and second multipurpose channels are in communication with a plurality of assay stations via the first and second assay station channels, respectively, of said plurality of assay stations.

6. The apparatus according to claim 5 wherein said plurality of assay stations are arranged to provide at least one of simultaneous or sequential filling of said plurality of assay stations with said sample fluid solution conducted thereto.

7. The apparatus according to claim 5 wherein said plurality of assay stations are arranged to provide at least one of simultaneous or sequential filling of said first and second multipurpose channels with said isolation medium to seal said plurality of assay stations.

8. The apparatus according to claim 2 wherein said at least a portion of said at least one first assay station channel has a cross-sectional area that is less than the cross-sectional area of at least a portion of said at least second assay station channel.

9. The apparatus of claim 1 wherein said first multipurpose channel surface characteristic conducive to conduction of said sample fluid comprises at least one of internal surface characteristic and/or shape characteristic and said at least one second multipurpose channel surface characteristic that is not-conducive to conduction of said sample fluid comprises at least one of an internal surface portion and/or shape characteristics.

10. The apparatus according to claim 1 wherein the apparatus further comprises a sealing layer sealing at least one assay station.

11. The apparatus of claim 10 wherein at least a portion of at least one of said assay station, first multipurpose channel and second multipurpose channel is formed in the substrate layer and at least a portion of at least one of said assay station, first multipurpose channel and second multipurpose channel is formed in the sealing layer.

12. The apparatus according to claim 1 wherein the internal surface of said first multipurpose channel permits flowthrough of at least one of a sample fluid, air and an isolation medium.

13. The apparatus according to claim 1 wherein the internal surface of said second multipurpose channel permits the flowthrough of at least one of air or an isolation-medium.

14. The apparatus of claim 1 wherein at least a portion of said assay station, first multipurpose channel and second multipurpose channel are formed in the substrate layer.

15. The apparatus of claim 1 wherein said at least one assay station has disposed therein at least one reaction assay component.

16. The apparatus of claim 1 wherein said sample fluid inlet is in communication with a sample fluid preparation element.

17. The apparatus of claim 16 further comprising at least one of a sample preparation chamber and a lid.

18. The apparatus of claim 17 wherein said sample preparation chamber further comprises an absorbent.

19. The apparatus of claim 1 further comprising at least one element for controlling fluid flow in at least one of said channels.

20. The apparatus according to claim 19 wherein said at least one flow controlling element is disposed between said sample preparation chamber and said at least first multipurpose channel.

21. The apparatus according to claim 19 said at least one flow controlling element is disposed adjacent said at least one assay station.

22. The apparatus of claim 1 further comprising a chamber for introduction of flow-promoting fluid.

23. The apparatus of claim 22 wherein at least one of said chamber or an inlet is in communication with a mixing chamber for mixing said flow-promoting fluid with said sample fluid.

24. The apparatus according to claim 1 wherein said at least one assay station comprises at least one component of an assay reaction pre-loaded therein.

25. The apparatus according to claim 24 wherein said least one component of said assay reaction at said at least one assay station provides at least one of detectable qualitative or quantitative data.

26. The apparatus of claim 25 further comprising beads having said at least one component of said assay reaction.

27. The apparatus according to claim 24 wherein said at least one component of said assay reaction is secured to said at least one assay station.

28. The apparatus according to claim 1 further comprising an absorbent in communication with a terminal portion of at least one of said at least first and second multipurpose channels.

29. The apparatus according to claim 28 wherein said absorbent is removeably attached to the terminal portion of said at least first and second multipurpose channels.

30. The apparatus according to claim 1 wherein said at least one assay station is further comprised of flow promoting structures.

31. The apparatus according to claim 1 wherein exposed portions of the said at least first second multipurpose channels are sealed with a solidifiable sealant adhesively, mechanically, electrically, or magnetically after the first and second multipurpose channels are filled with a sample fluid and/or an isolation medium.

32. The apparatus of claim 1, wherein said flow of said isolation medium is by virtue of said at least one surface characteristic of said at least one first multipurpose channel and said at least one surface characteristic of said at least one second multipurpose channel.

33. The apparatus of claim 1, wherein said sample fluid inlet serves as an isolation medium outlet to enable the isolation medium to flow out of said first multipurpose channels.

34. A method for conducting reactions on the apparatus of claim 1 comprising;
   obtaining a sample fluid;
   introducing a sample fluid to the at least one sample inlet;
   filling said at least one assay station via said at least one multipurpose channel with said sample fluid;
   allowing isolation medium from said at least one isolation medium inlet to flow into at least said first multipurpose channel; and
   running at least one reaction at said at least one assay station, said reaction providing at least one of qualitative or quantitative data relating to said sample fluid.

35. The method according to claim 34 further comprising running said at least one reaction under temperature control.

36. The method according to claim 34 further comprising the step of obtaining said sample fluid from a test sample.

37. The method according to claim 36 further comprising the step of subjecting said test sample to at least one preparative operation.

38. The method according to claim 37 further comprising performing said at least one preparative operation separately from said substrate.

39. The method according to claim 37 further comprising performing said at least one preparative operation at least one of upon or within said substrate.

40. The method according to claim 37 wherein said at least one preparative operation provides nucleic acids susceptible for use in said at least one reaction.

41. The method according to claim 37 wherein the step of obtaining said sample fluid includes at least one preparative operation in a sample preparation chamber, comprising at least one of exposing said test sample to a lysing buffer, elution buffer and a washing buffer, in order to obtain said sample fluid.

42. The method according to claim 41 further comprising adding a flow promoting fluid to said sample fluid.

43. The method according to claim 41 wherein said at least one preparation operation is conducted upon said substrate, further comprising the step of agitating said substrate in order to promote the entry of nucleic acids, contained in a nucleic acid containing test sample, to enter into said sample fluid.

44. The method of claim 43 wherein said step of agitating said substrate is performed by agitating said substrate at the resonant frequency of at least one of said substrate and the sample fluid contained in said sample preparation chamber.

45. The method of claim 43 wherein said agitating step is performed by agitating electro-magnetically magnetic beads in said sample preparation chamber.

46. The method of claim 43 further comprising heating said elution buffer contained in said filtration chamber to generate a thermal-gradient induced convection flow, and causing more nucleic acid molecules to enter into solution.

47. The method of claim 46 further comprising a step of adding surfactant to said elution buffer contained in a said sample preparation chamber.

48. The method of claim 36 wherein said test sample is at least one of homogenized, digested and filtered before injection into said sample introduction inlet.

49. The method according to claim 34 wherein said at least one of qualitative or quantitative data provides at least one of a colorimetric, flurometric or luminescent result.

50. The method of claim 34 further comprising the step of disposing at least one assay reaction component into said at least one assay station.

51. The method according to claim 34 wherein said step of running said at least one reaction comprises nucleic acid amplification.

52. The method according to claim 51 further comprising the step of exposing said at least one assay station to irradiation.

53. The method of claim 34 further comprising obtaining said at least one of qualitative or quantitative data utilizing fluorescence.

54. The method according to claim 53 wherein said fluorescence is provided by at least one of binding of a fluorophore or hybridization of fluorophore containing probe.

55. The method according to claim 34 wherein said qualitative or quantitative data is obtained via probe labeled with at least one of a fluorophore, an enzyme or component of a binding complex.

56. The method according to claim 55 further comprising introducing sequentially said isolation medium into said at least first and second multipurpose channels.

57. The method according to claim 34 further comprising the step of displacing said sample fluid via isolation medium.

58. The method according to claim 57 wherein said isolation medium is first introduced into said at least first multipurpose channel followed by introduction into said at least second multipurpose channel.

59. The method according to claims 56 or 58 wherein said introduction of isolation medium provides the purging or air from said at least second multipurpose channel and the purging of said sample fluid from said at least first multipurpose channel, resulting in the isolation of said at least one assay station containing said sample fluid.

60. The method according to claim 34 further comprising the step of at least of solidifying, curing and polymerizing said isolation medium.

61. The method according to claim 34 wherein exposed portions of the said at least first and second multipurpose channels are sealed with a solid from ambient atmosphere adhesively, mechanically, or magnetically after the first and second multipurpose channels are filled with sample fluid and/or isolation medium.

62. The method according to claim 34 further comprising heating said fluid sample prior to filling said at least one assay station.

\* \* \* \* \*